United States Patent
Fan

(10) Patent No.: US 9,795,570 B2
(45) Date of Patent: Oct. 24, 2017

(54) MODULATION OF MACROPHAGE PHENOTYPE BY EMODIN

(71) Applicant: University of South Carolina, Columbia, SC (US)

(72) Inventor: Daping Fan, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/458,560

(22) Filed: Mar. 14, 2017

(65) Prior Publication Data
US 2017/0266131 A1    Sep. 21, 2017

Related U.S. Application Data

(60) Provisional application No. 62/309,576, filed on Mar. 17, 2016.

(51) Int. Cl.
*A61K 31/12* (2006.01)
*A61K 31/122* (2006.01)

(52) U.S. Cl.
CPC .................. *A61K 31/122* (2013.01)

(58) Field of Classification Search
CPC ..................................................... A61K 31/12
USPC ......................................................... 514/680
See application file for complete search history.

(56) References Cited

U.S. PATENT DOCUMENTS

| | | |
|---|---|---|
| 4,522,811 A | 6/1985 | Eppstein et al. |
| 8,734,859 B1 | 5/2014 | Shraibom |
| 2003/0125265 A1 | 7/2003 | Hung et al. |
| 2006/0115834 A1 | 6/2006 | Racila et al. |
| 2007/0117784 A1 | 5/2007 | Cleland et al. |
| 2010/0081724 A1* | 4/2010 | Arigony Souto ...... A61K 36/70 514/680 |
| 2012/0122807 A1* | 5/2012 | Shraibom .......... A61K 31/7048 514/26 |
| 2013/0045933 A1* | 2/2013 | Fridman .............. C07H 15/244 514/25 |

FOREIGN PATENT DOCUMENTS

WO    WO2011089602 A2    7/2011

OTHER PUBLICATIONS

Jelassi, Bilel, et al. "Anthraquinone emodin inhibits human cancer cell invasiveness by antagonizing P2X7 receptors." *Carcinogenesis* (2013): bgt099.
Shrimali, Deepti, et al, "Targeted abrogation of diverse signal transduction cascades by emodin for the treatment of inflammatory disorders and cancer," *Cancer letters* 341.2 (2013): 139-149.

* cited by examiner

*Primary Examiner* — Raymond Henley, III
(74) *Attorney, Agent, or Firm* — Dority & Manning, PA

(57) ABSTRACT

Methods and materials that can be used to regulate macrophage activation are described. Methods can utilize emodin to bi-directionally modulate macrophage activation and return macrophage phenotype to a homeostatic center (e.g., between M1 and M2 phenotypes) in various environmental settings. Methods can target multiple pathologies within a same individual. Methods can be utilized to inhibit macrophage phenotype activation and affect downstream response to phenotype inducing stimulus, thereby altering macrophage memory.

20 Claims, 14 Drawing Sheets

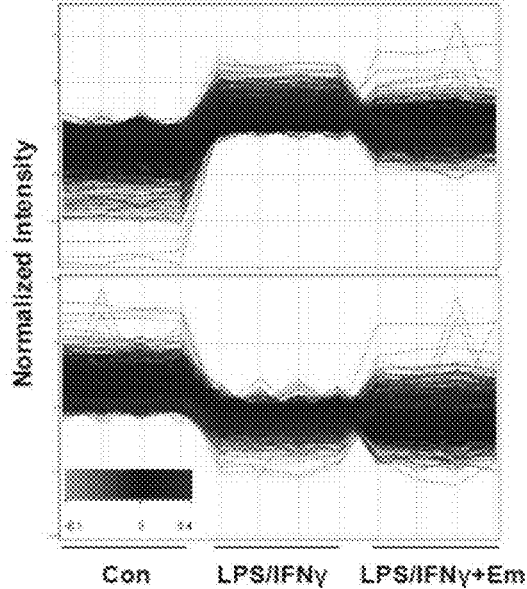
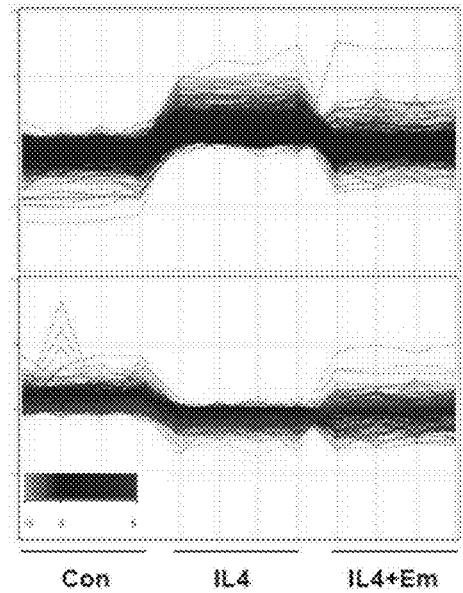
FIG. 1A
FIG. 1B
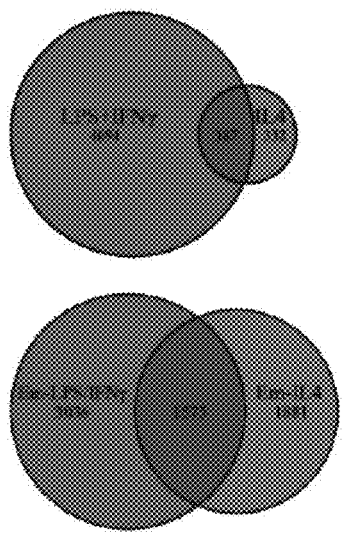
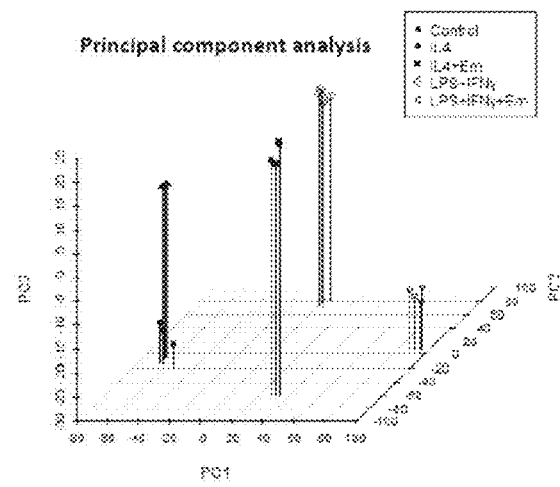
FIG. 1C
FIG. 1D

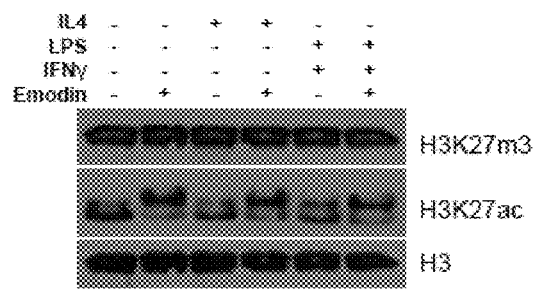
FIG. 6A
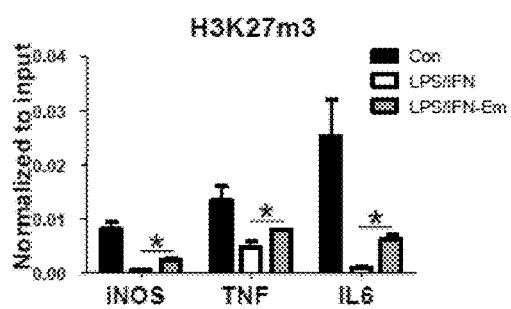
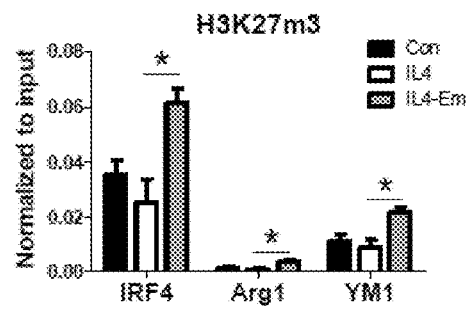
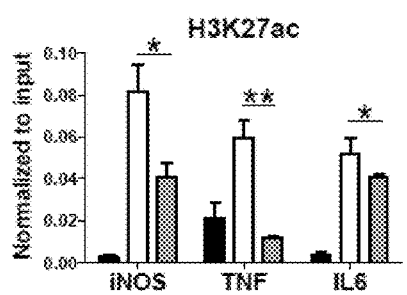
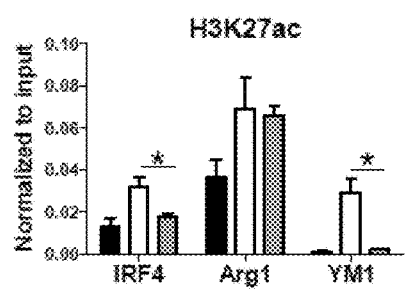
FIG. 6B                    FIG. 6C

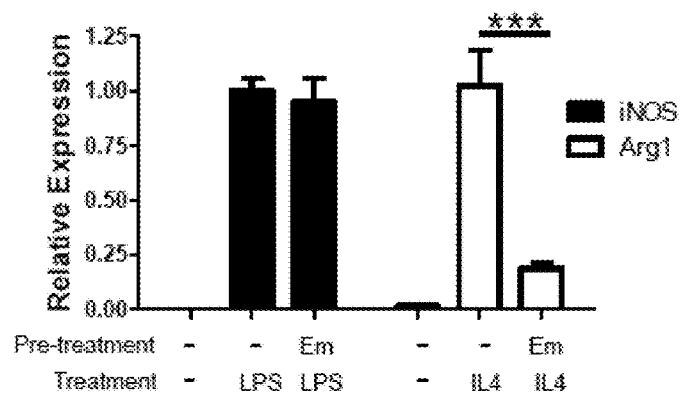
FIG. 8B
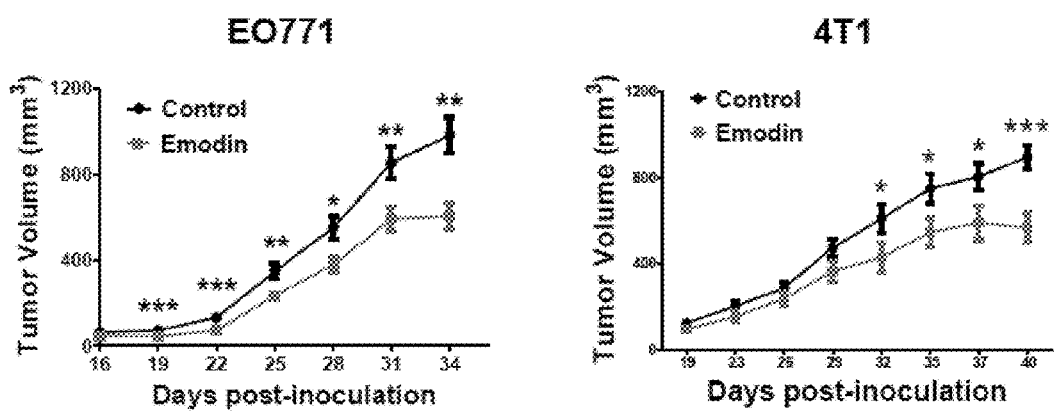
FIG. 9A  FIG. 9C
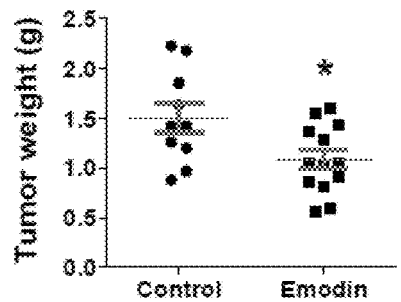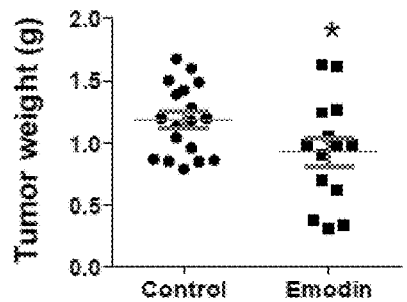
FIG. 9B  FIG. 9D

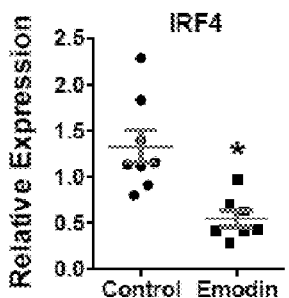
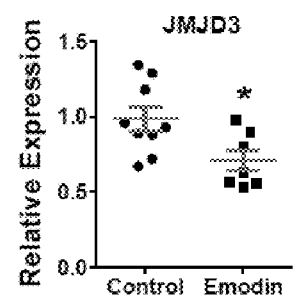
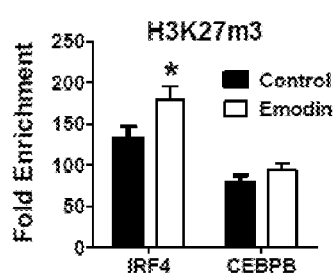
FIG. 10D
FIG. 10E
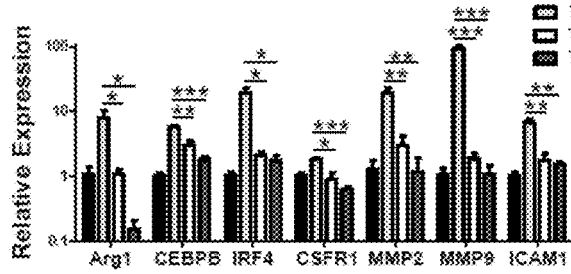
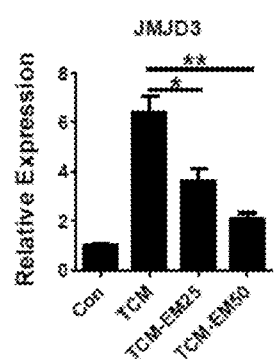
FIG. 11A
FIG. 11B
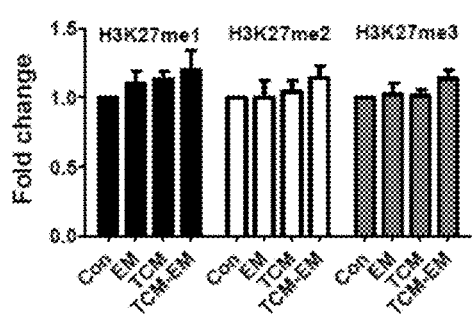
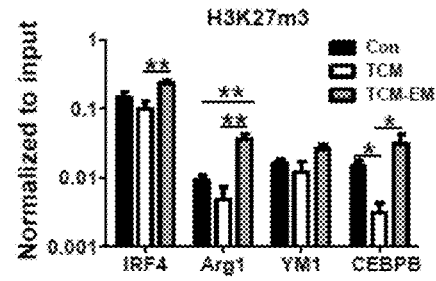
FIG. 11C
FIG. 11D

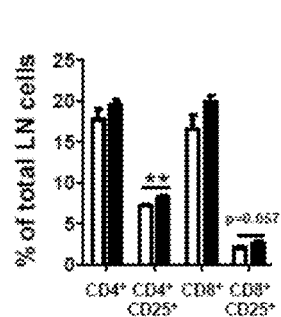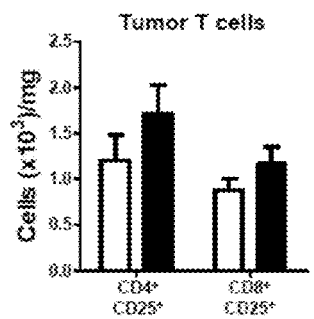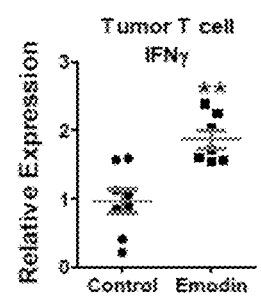
FIG. 12A              FIG. 12B              FIG. 12C
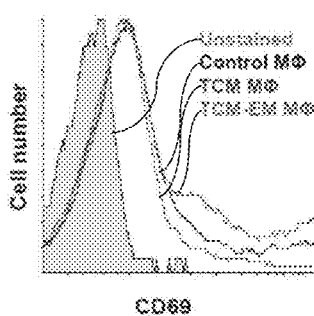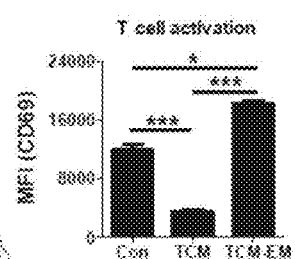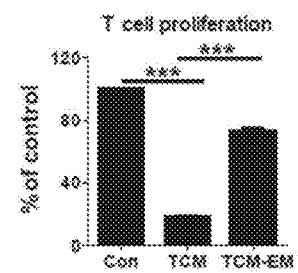
FIG. 12D              FIG. 12E
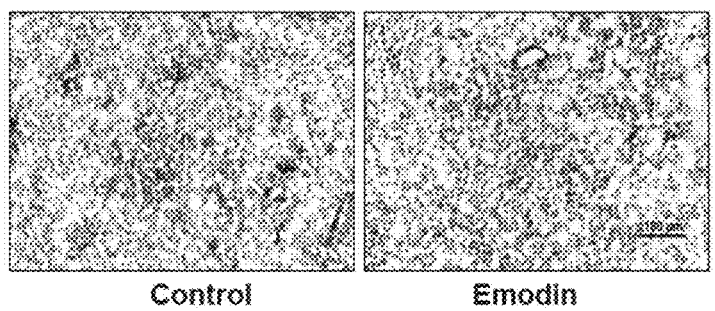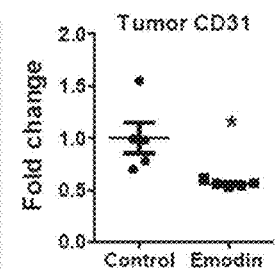
FIG. 12F

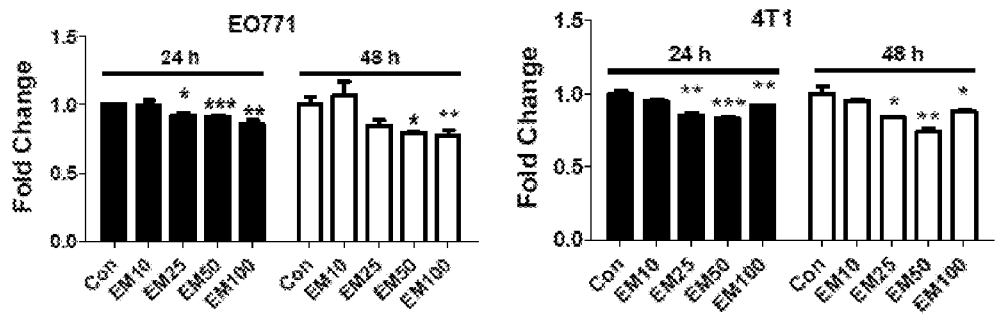
FIG. 13A
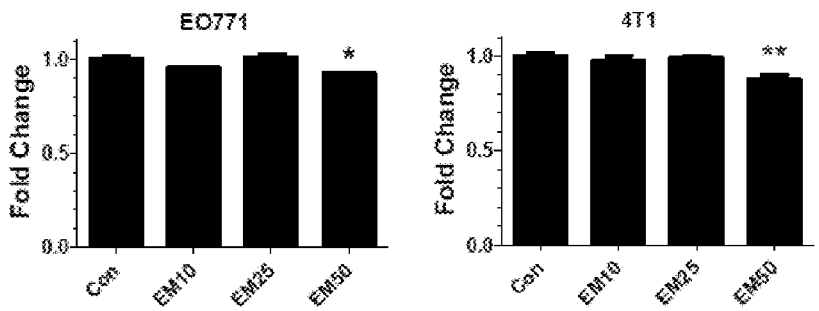
FIG. 13B
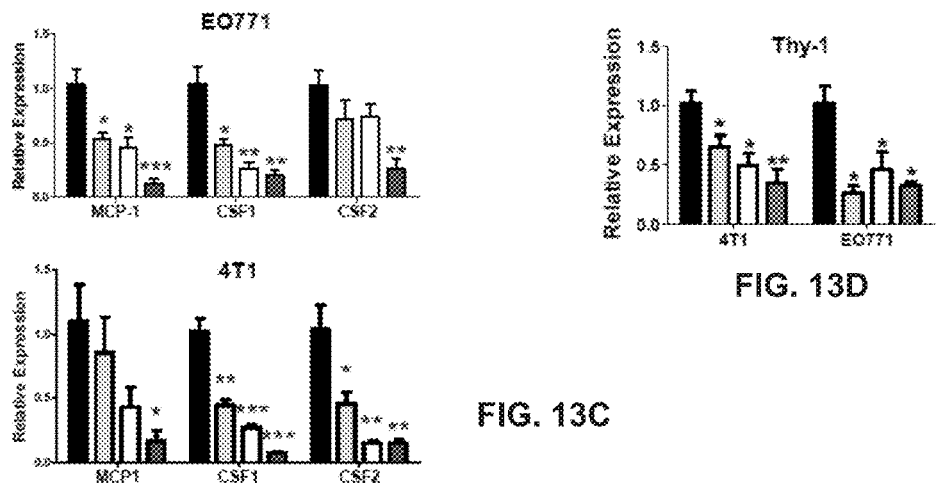
FIG. 13C
FIG. 13D

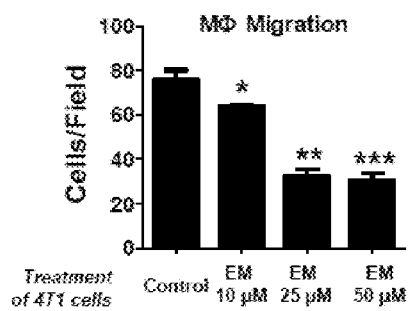
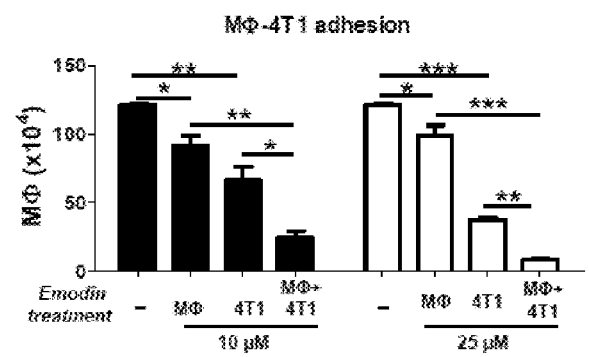
FIG.14A   FIG. 14B
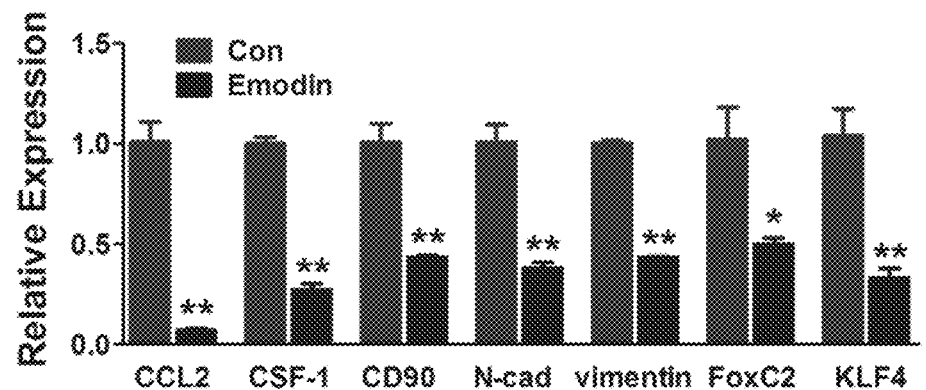
FIG. 15

MODULATION OF MACROPHAGE PHENOTYPE BY EMODIN

CROSS REFERENCE TO RELATED APPLICATION

This application claims filing benefit of U.S. Provisional Patent Application Ser. No. 62/309,576 having a filing date of Mar. 17, 2016, which is incorporated herein by reference.

GOVERNMENT SUPPORT CLAUSE

This invention was made with government support under HL116626 and AT003961-8455 awarded by the National Institutes of Health. The government has certain rights in the invention.

BACKGROUND

Macrophages include a heterogeneous population of cells found in most tissues of the body. These cells are capable of performing a broad spectrum of functions. Macrophage phenotypes are classified along a continuum between the extremes of pro-inflammatory M1 macrophages and anti-inflammatory M2 macrophages.

Macrophages are induced to a pro-inflammatory M1 state by Th1 cytokines (such as IFNγ and TNFα) and bacterial products (such as LPS). M1 macrophages play major roles in host defense against bacteria and tissue remodeling post-injury through production of pro-inflammatory cytokines (such as IL12, TNFα, and IL1), reactive oxygen species (ROS) and nitric oxide (NO), and proteases (such as MMP 2 and 9). A combination of stimuli including Th2 cytokines (such as IL4, IL10 and IL13), growth factors (such as TGFβ and CSF1), glucocorticoids, and immune complexes, can polarize macrophages toward an anti-inflammatory M2 phenotype. M2 macrophages play major roles in tissue homeostasis and repair, inflammation resolution, and immune regulation.

The seemingly opposing functions of M1 and M2 macrophages must be tightly regulated for an effective and proper response to foreign molecules or damaged tissue. Excessive activation of either M1 or M2 macrophages contributes to the pathology of many diseases. For instance, chronic M1 macrophage activation promotes tissue damage in neurodegenerative disorders, arthritis, and autoimmune diseases. While necessary for the initial stages of tissue repair, an excessive M1 activation inhibits the healing of damaged tissue through excessive matrix degradation and inhibition of tissue regeneration. Chronic M1 activation has also been shown to promote the development of cancer. Increased inflammatory monocyte/macrophage infiltration has been shown to correlate with disease severity for patients with myocardial infarction, atherosclerosis, and metabolic disorders.

Prolonged or excessive M2 macrophage activation has also been shown to be detrimental. M2 macrophages contribute to lung inflammation and damage in allergy and asthma. They have also been shown to impair tissue functions through promoting fibrosis. M2 macrophage infiltration correlates with increased cancer growth and metastasis in multiple types of cancer. They are shown to promote cancer growth and metastasis by supporting ECM remodeling, angiogenesis, and immune suppression.

Macrophage infiltration has been correlated with severity in many types of cancer. Tumor cells recruit macrophages and educate them to adopt an M2-like phenotype through the secretion of chemokines and growth factors, such as MCP1 and CSF1. Macrophages in turn promote tumor growth through supporting angiogenesis, suppressing anti-tumor immunity, modulating extracellular matrix remodeling, and promoting tumor cell migration. Thus tumor cells and macrophages interact to create a feedforward loop supporting tumor growth and metastasis. For instance, breast cancer tumor growth and metastasis depend on the support from stromal cells, including macrophages, fibroblasts, and myeloid-derived suppressor cells (MDSCs) in the tumor microenvironment (TME) which promote angiogenesis, matrix remodeling, and immunosuppression.

Macrophages are also able to retain a memory for the signals that they have been exposed to through epigenetic modification, which results in increased transcription (priming) or repressed transcription (tolerance) upon future exposure. Cytokines cause the epigenetic modification through addition of positive histone modifications H3K4m3 or H3K27ac to gene promoters, which lead to increased expression. The mechanisms of tolerance are incompletely understood but are believed to involve the loss of positive histone modifications and/or an increase in negative histone modifications (such as H3K27m3).

There has been growing interest in immunotherapies for the treatment of cancers including breast cancer because of their low toxicity and extended duration of action. Unfortunately, the immunosuppressive microenvironment of tumors greatly diminishes the effectiveness of these therapies. MDSCs, M2-like tumor-associated macrophages (TAMs), and regulatory T cells have all been shown to repress an effective anti-tumor immune response through the production of anti-inflammatory cytokines and growth factors such as IL10 and TGFβ. Therapies targeting the immunosuppressive microenvironment have shown great potential on their own or in combination with other therapies in experimental models.

There has also been growing interest in herb derived compounds as they can modulate multiple inflammatory pathways, are inexpensive, and have low toxicity for chronic treatment. Emodin is a trihydroxy-anthraquinone which is found in several Chinese herbs including rhubarb (*Rheum palmatum*) and tuber fleece flower (*Polygonam multiflorum*, also commonly known as Chinese knotweed or he shou wu). Emodin has shown potential to inhibit inflammation in various settings. For instance, emodin has been shown to attenuate the severity of experimental disease models including arthritis, liver damage, atherosclerosis, myocardial ischemia, and cancer.

What are needed in the art are methods and materials that can inhibit a broad range of macrophage phenotypes through regulation of multiple signaling pathways. Such a compound would have great clinical potential.

SUMMARY

According to one embodiment, disclosed is a method for promoting macrophage homeostasis. For instance, a method can include delivering emodin to an area that includes macrophages and at least one macrophage phenotype inducing stimulus (e.g., M1 and/or M2 phenotype inducing stimuli). The emodin can suppress the response of the macrophages to the stimuli and can restore or maintain homeostasis of the macrophages between multiple different macrophage phenotypes.

Also disclosed is a method for preventing macrophage response to a phenotype inducing stimulus. For instance, a method can include delivering emodin to an area that includes a macrophage and a macrophage phenotype inducing stimulus. At a later time, the macrophage can be exposed a second time to a macrophage phenotype inducing stimulus that can be the same or different as the first stimulus. At the second exposure the response of the macrophage to the stimulus can be decreased as compared to response of a non-emodin treated macrophage.

Also disclosed is a method for preventing macrophage migration. According to this embodiment, a method can include delivering emodin to an area that includes macrophages, cancer cells, and at least one M2 phenotype inducing stimulus. The emodin can suppress the response of the macrophages to the stimulus and can thereby prevent migration of the macrophages toward the cancer cells or toward distant organs.

BRIEF DESCRIPTION OF THE DRAWINGS

The present invention may be better understood with reference to the accompanying figures, in which:

FIG. 1A illustrates the results of stimulation of mouse peritoneal macrophages with LPS (100 ng/ml) and IFNγ (20 ng/ml) for 24 h with or without emodin (50 μM). Gene expression was detected using a whole genome microarray. Genes shown were significantly increased (top panel) or decreased (bottom panel) in expression. Y-axis corresponds to normalized intensity values for gene expression and x-axis to treatments. Each line represents one gene.

FIG. 1B illustrates the results of stimulation of mouse peritoneal macrophages with IL4 (10 ng/ml) for 6 h with or without emodin (50 μM). Gene expression was then detected using a whole genome microarray. Genes shown were significantly increased (top panel) or decreased (bottom panel) in expression. Y-axis corresponds to normalized intensity values for gene expression and the x-axis to treatments. Each line represents one gene.

FIG. 1C presents Venn diagrams showing genes significantly changed by LPS/IFNγ and IL4 and by emodin under LPS/IFNγ or IL4 stimulation.

FIG. 1D presents a principle component analysis of genes significantly changed in one of the treatment groups.

FIG. 6A illustrates global histone modification following emodin inhibition of LPS/IFNγ and IL4 induced histone modifications in macrophages. Macrophages were stimulated with LPS (100 ng/ml) and IFNγ (20 ng/ml) or IL4 (10 ng/ml) with or without emodin (50 μM) for 24 h. Levels were detected using western blotting. Experiment was performed in triplicate (n=3).

FIG. 6B graphically illustrates ChIP-PCR results for detection of H3K27m3 and H3K27ac modifications upon inhibition of LPS/IFNγ induced activation. Results are shown as the mean±SE (n=3). $*p≤0.05$; $**p≤0.01$.

FIG. 6C graphically illustrates ChIP-PCR results for detection of H3K27m3 and H3K27ac modifications upon inhibition of IL4 induced activation. Results are shown as the mean±SE (n=3). $*p≤0.05$; $**p≤0.01$.

FIG. 8B graphically illustrates results following incubation of macrophages with or without emodin (50 μM) for 24 h. Following initial emodin treatment the cells were washed and incubated for 2 d and further stimulated with either IL4 or LPS for 6 h and the gene expression was analyzed with qPCR. Results are shown as the mean±SE for two independent experiments (n=3). $*p \leq 0.05$; $**p \leq 0.01$.

FIG. 9A illustrates tumor response following injection of C57Bl/6 (n=7 for control, n=8 for emodin group) with 2×10$^5$ EO771 cells. Emodin treatment (40 mg/kg IP once daily) began on Day 1 following tumor injection of tumor cells.

FIG. 9B presents the weight of tumors described in FIG. 9A.

FIG. 9C illustrates results following injection of Balb/c (n=9 for control, n=7 for emodin group) with 2×10$^5$ 4T1 cells. Emodin treatment (40 mg/kg IP once daily) began on Day 1 following tumor injection of tumor cells. For both FIG. 9A and FIG. 9B tumor size was measured with calipers and volume was calculated using the following formula: $V (mm^3) = L \times W^2 / 2$.

FIG. 9D presents the weight of tumors described in FIG. 9C. For all of FIG. 9A-FIG. 9D $*p<0.05$, $p<0.01$, $*p<0.001$ versus control.

FIG. 10D presents results for gene expression (n=9 for control, n=7 for emodin group) detected using RT-qPCR. F4/80+ TAMs were isolated from 4T1 tumors at the experimental endpoint using magnetic beads.

FIG. 10E presents H3K27m3 levels detected by a ChIP assay on the promoters of IRF4 and C/EBPβ (n=8 for control, n=6 for emodin group). Results are shown as means±S.E. $*p<0.05$, $***p<0.001$, versus control.

FIG. 11A presents results of gene expression determination measured using RT-qPCR, n=3. Peritoneal macrophages from C57Bl/6 mice were stimulated with EO771 tumor conditioned medium (TCM) with or without emodin for 24 h. Results are shown as mean±S.E of one of two independent experiments.

FIG. 11B presents results of JMJD3 of gene expression measured using RT-qPCR, n=3. Peritoneal macrophages from C57Bl/6 mice were stimulated with EO771 TCM with or without emodin at either 25 μM or 50 μM for 24 h. Results are shown as mean±S.E of one of two independent experiments.

FIG. 11C presents results of histone modification detection. Histones were extracted from the macrophages and histone modifications were detected using an EpiQuick histone modification kit, n=3.

FIG. 11D presents the change levels of gene specific H3K27m3. Levels were examined using a ChIP assay. Results are shown as mean±S.E. of one of two independent experiments, n=3. $*p<0.05$, $p<0.01$, $*p<0.001$.

FIG. 12A illustrates the ability of emodin to attenuate the effects of macrophages on T cell activation and angiogenesis at the lymph nodes.

FIG. 12B illustrates the ability of emodin to attenuate the effects of macrophages on T cell activation and angiogenesis at tumors. The lymph nodes of FIG. 12A and tumors of FIG. 12B were obtained from mice bearing 4T1 tumors (n=9 for control, n=7 for emodin group). The tissues were collected at the experimental endpoint. A single cell suspension was made, and the cells were stained with CD3, CD4 or CD8, and CD25 to detect activated T cells. Cells were analyzed using flow cytometry. Results are shown as means±S.E.

FIG. 12C presents the expression of IFNγ from CD3+ T cells that were isolated from the draining lymph nodes of mice bearing 4T1 tumors 6 weeks after tumor cell injections. Expression of IFNγ was detected using RT-qPCR.

FIG. 12D presents the results of examination of peritoneal macrophages from C57Bl/6 mice treated with EO771 TCM with or without emodin for 24 h. Following treatment, the macrophages were washed and co-cultured with T cells isolated from the spleens of mice and stimulated with CD3/CD20 microbeads at a ratio of 1:1. After 24 h, the T cells were collected and stained with CD3, CD4, and CD69 and analyzed using flow cytometry. Left panel shows representative flow cytometry results. Right panel shows results as mean±S.E. (n=3).

FIG. 12E presents the results of examination of macrophages pre-treated with TCM with or without emodin for 24 h. Following treatment, the macrophages were washed and co-cultured with CSFE-labeled T cells and stimulated with CD3/CD20 microbeads. After 72 h, the cells were collected and stained for CD3 and CD4, and CSFE depletion was detected as a measure of proliferation. Results are shown as mean±S.E. of one of two independent experiments, n=3.

FIG. 12F presents images of EO771 tumors collected from mice 5 weeks post injection and embedded in OCT. The tumors (n=5) were cut into 8 μm thick sections, stained with CD31, and imaged (200×, 10 fields per section). Images were quantified using ImagePro plus by calculating the IOD for CD31 positive areas. Quantified results (right panel) are shown as means±S.E. *p<0.05, p<0.01, *p<0.001.

FIG. 13A illustrates the effects of emodin on breast cancer cells. Tumor cells were treated with emodin (0-100 μM) for 24-48 h. Cell viability was determined using an LDH assay. Results are shown as mean±S.E. for one of two independent experiments, n=4.

FIG. 13B illustrates the results for tumor cells stained for Ki67 after 24 h culture. Cells were then analyzed using flow cytometry. Results are shown as mean±S.E., n=4.

FIG. 13C presents the results of gene expression analysis 24 h post-treatment, gene expression was examined using qPCR. Results are shown as mean±S.E. of one of two independent experiments, n=3. *p<0.05, p<0.01, *p<0.001, versus control.

FIG. 13D presents the results of gene expression analysis 24 h post-treatment, gene expression was examined using qPCR. Results are shown as mean±S.E. of one of two independent experiments, n=3. *p<0.05, p<0.01, *p<0.001, versus control.

FIG. 14A illustrates migration of 4T1 cells following treatment with emodin for 24 h. Following treatment, the cells were washed and cultured in fresh medium for 48 h. Conditioned medium was collected from the cells and placed in the bottom chamber of transwell inserts. Peritoneal macrophages were placed in the top and incubated for 4 h. The cells were then fixed and the membranes were mounted onto slides and imaged (200×, 5 fields per membrane). The cells that migrated to the bottom chamber were counted. Results are shown as mean±S.E. of one of two independent experiments, n=3.

FIG. 14B illustrates adhesion of peritoneal macrophages from Balb/c mice and/or 4T1 cells treated with emodin for 24 h. Following treatment, the macrophages were collected and seeded onto 4T1 cell monolayers. After 1 h, non-adherent cells were washed away and the remaining cells were collected and counted. Cells were then stained with F4/80 and analyzed using flow cytometry. Results are shown as mean±S.E., n=3. *p<0.05, p<0.01, *p<0.001.

FIG. 15 graphically illustrates the decrease in expression of several genes following treatment of ex vivo breast tumor cells with emodin.

DETAILED DESCRIPTION

Figure 2:
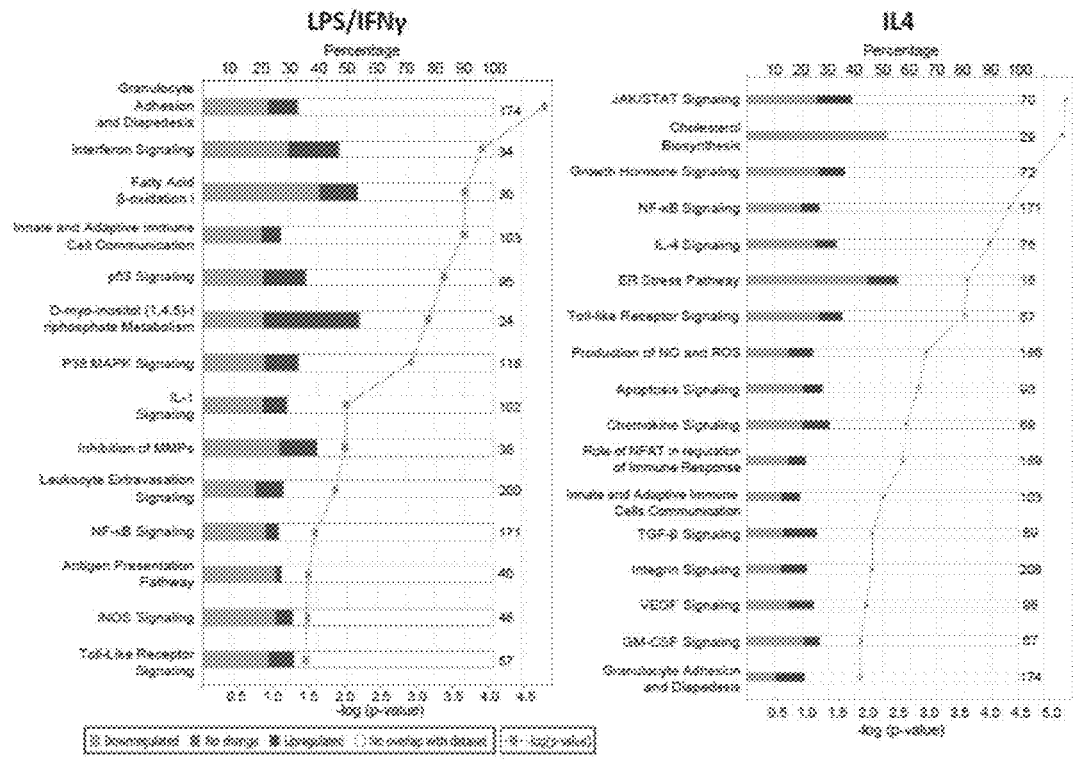
FIG. 2 graphically illustrates inhibition by emodin of the induction of signaling pathways associated with macrophage polarization and function. Most significantly affected pathways relevant for macrophage activation were determined by Ingenuity IPA canonical pathway analyses.

The following description and other modifications and variations to the presently disclosed subject matter may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only, and is not intended to limit the disclosed subject matter.

In general, disclosed herein are methods and materials that can be used to regulate macrophage activation. More specifically, disclosed methods and materials incorporate the herb-derived trihydroxy-anthraquinone emodin to control macrophage activation. Beneficially, it has been discovered that emodin can bi-directionally modulate macrophage activation by targeting multiple pathways. For instance, emodin can be utilized to return macrophage phenotype to the homeostatic center between the extremes of M1 or M2 in various environmental settings. Moreover, emodin can inhibit both M1 and M2 polarization of macrophages through both transcriptional and epigenetic regulation. As such, emodin can be utilized in a wide variety of applications as it can regulate a subset of genes depending on the particular stimulus, pushing the phenotype of the cell back toward the center of the two poles. Emodin can exhibit more profound effects on M2 polarization in some applications, suggesting emodin can be highly beneficial for patients with M2 macrophage-driven diseases. However emodin can exert different homeostasis maintaining effects on macrophages in different locations and environments and thus in one embodiment can target multiple different macrophage related pathologies within a same individual. By way of example, disclosed methods and materials can be utilized in treatment of one or more macrophage related pathologies including, without limitation, neurodegenerative disorders, arthritis, autoimmune diseases, tissue repair (e.g., wound healing including chronic wounds, surgical wounds, etc.), cancer, myocardial infarction, atherosclerosis, metabolic disorders, and lung inflammation and damage such as found in allergy and asthma.

In one embodiment, disclosed materials can be used to maintain macrophage homeostasis by inhibiting activation of macrophage to any of a variety of different phenotypes by phenotype inducing stimuli as are known in the art. In one particular embodiment, emodin can be utilized to control M1 and/or M2 activation and thereby maintain macrophage homeostasis and prevent over-activation in either a pro-inflammatory or anti-inflammatory direction. As described further herein, emodin can inhibit the change in expression of a large percentage of both M1 and M2 associated genes. For example, emodin can inhibit an excessive or chronic M1 activation pathway, e.g., the NFkB, IRF5 and/or STAT1 pathways, as may be induced by Th1 cytokines (e.g., LPS and IFNγ stimulation) and/or bacterial products (e.g., LPS stimulation) as are known in the art. Moreover, emodin can simultaneously or alternatively be utilized to inhibit an excessive or chronic M2 activation pathway, e.g., the STAT6 and/or IRF4 signaling pathways as may be induced by IL4 stimulation. Emodin can suppress the response of macrophages to other phenotype inducing stimuli including, without limitation, Th1 cytokines (such as IFNγ and TNFα), bacterial products (such as LPS), Th2 cytokines (such as IL4, IL10 and IL13), growth factors (such as TGFβ and CSF1), glucocorticoids, and immune complexes.

Bi-directional control of macrophage activation by use of emodin can be utilized to control macrophage functions such as phagocytosis, migration, and NO production. For instance, emodin can bi-directionally tune the induction of LPS/IFNγ and IL4 responsive genes through inhibiting NFkB/IRF5/STAT1 signaling and IRF4/STAT6 signaling, respectively; and thereby emodin can modulate macrophage phagocytosis, migration, and NO production.

Cytokines such as IFNγ can prime genes for increased expression by the recruitment of transcription promoting histone markers (such as H3K4m3, H3K9m3 and H3K27ac) to the promoter or enhancer regions. H3K27me3 attenuates M2 polarization by inhibiting the expression of IRF4; therefore, its removal by demethylase JMJD3 promotes M2 activation. H3K27ac has been shown to prime both M1 and M2 genes for expression upon subsequent stimulation. Emodin can significantly change the expression of several histone modifying enzymes, particularly those responsible for regulating H3K27 tri-methylation and acetylation. Emodin appears to have no effect on genome wide levels of H3K27ac and H3K27m3; however, it can significantly increase H3K27m3 levels while decreasing H3K27ac levels on the promoters of many M1 and M2 genes following treatment.

This can provide a route for emodin to be utilized to regulate macrophage memory by inhibiting changes in H3K27m3 and H3K27ac at the promoter regions of several key genes. Initial stimulation of macrophages with a macrophage stimulating compound such as IFNγ can result in an enhanced response to the same or different macrophage stimulating compounds at a later time. However, emodin co-treatment during an initial stimulation can significantly diminish the exaggerated responses even though gene expression can return to near baseline levels prior to second stimulation. Data suggest that at least part of emodin's effects on macrophage activation and memory can be attributed to gene specific epigenetic modifications.

Overall, it has been found that emodin is able to suppress excessive response of macrophages to multiple stimuli, e.g., both M1 and M2 stimuli, and as such disclosed methods and materials can restore macrophage homeostasis in various pathologies, and in particular in pathologies driven by or involving an imbalance in macrophage activation and polarization.

Without wishing to be bound to any particular theory, it is believed that the effects of emodin on macrophage polarization are due to directly interacting with a combination of kinases/receptors depending on the microenvironment to which the cells are exposed. Emodin can target different transcriptional networks in different stimulation settings, indicating emodin's ability to differentially affect a broad-spectrum of signaling pathways depending on the microenvironment. For instance, emodin can inversely regulate multiple genes including, but not limited to, Mrc1, YM1, TNFα, CXCL2, and CXCL10 in macrophages. Emodin can inhibit numerous signaling pathways including, but not limited to NFκB, STAT1, and IRF5 as may be stimulated by LPS/IFNγ, and STAT6 and IRF4 as may be stimulated by IL4.

Emodin can regulate the IRF signaling pathways. IRF4 and IRF5 have previously been shown to be inversely regulated pushing macrophages toward an M2 or M1 phenotype, respectively. IRF5 can be activated by TLR4 ligation and can promote the transcription of pro-inflammatory genes (e.g. IL12b) while suppressing the expression of anti-inflammatory genes (e.g. IL10). IRF4 competitively binds to MyD88 and is a negative regulator of IRF5 signaling. IRF4 can be regulated through the removal of H3K27m3 by the histone demethylase JMJD3. Emodin can inhibit both IRF4 and IRF5 signaling.

In one embodiment, emodin can be beneficially utilized to inhibit breast cancer growth. More specifically, emodin can attenuate tumor growth by modulating the tumor microenvironment including inhibition of macrophage infiltration and M2-like polarization, accompanied by increased T cell activation and reduced angiogenesis in tumors. In this context, emodin can inhibit signaling pathways such as IRF4, STATE, and C/EBPβ and can increase inhibitory histone such as H3 lysine 27 tri-methylation (H3K27m3) on the promoters of M2 related genes in tumor-associated macrophages. Emodin can inhibit tumor cell-macrophage interactions through blocking the response of macrophages to tumor signals and by inhibiting the paracrine and juxtacrine signaling from tumor cells to macrophages. Through its effects on TAMs, emodin can effectively increase T cell activation and inhibit angiogenesis in breast cancer tumors. In addition, emodin can inhibit tumor cell-macrophage adhesion, at least partially, via suppressing Thy1 expression on tumor cells and ICAM1 expression on macrophages. Emodin can also inhibit tumor cell secretion of macrophage chemoattractant and growth factors MCP1, CSF1, and CSF2. Taken together, data show that emodin can block the pro-tumor feedforward loop between breast cancer cells and macrophages by targeting both cell types.

Without wishing to be bound to any particular theory, data suggest that emodin can activate T cells indirectly through inhibiting TAM-mediated immune suppression. TCM treated macrophages can significantly inhibit T cell activation and proliferation; however, emodin treatment can abrogate the suppressive ability of TCM treated macrophages. In addition, emodin can significantly inhibit the ability of tumor cells to attract and polarize macrophages through blocking the secretion of MCP1 and CSF1, two chemokines that play important roles in the TME. In addition, emodin can suppress ICAM1 expression in macrophages and Thy-1 expression in breast cancer cells, thus blocking the direct adhesion between these two cell types. Taken together, results indicate that emodin acts on both breast cancer cells and TAMs and thus ameliorates the immunosuppressive TME in breast cancer.

Emodin's ability to interfere with the communication between tumor cells and TAMs by a variety of mechanisms gives it great therapeutic potential to overcome these obstacles and as such emodin may be utilized in one particular embodiment as a potent therapy for breast cancer. Beneficially, emodin may be utilized in such an application in combination with other chemotherapies including immunotherapies or cancer cell targeting therapies as are known in the art.

In order for emodin to be effectively utilized in a clinical therapy, it can be delivered so as to be provided with suitable bioavailability. In general, emodin may be administered to a subject according to known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, emodin can be administered directly to the area of a tumor or cancer tissue, including administration directly to the tumor stroma during invasive procedures. Emodin may also be placed on a solid support such as a sponge or gauze for administration.

Emodin can be administered in conjunction with an accepted pharmaceutically acceptable carrier. Acceptable carriers include, but are not limited to, saline, buffered saline, glucose in saline. Solid supports, liposomes, nanoparticles, microparticles, nanospheres or microspheres may also be used as carriers for administration of emodin.

The appropriate dosage ("therapeutically effective amount") of the emodin can depend, for example, on the pathology to be treated, the severity and course of the pathology, whether the emodin is administered for preventive or therapeutic purposes, previous therapy, the patient's clinical history and response to the emodin, and the discretion of the attending physician, among other factors. Emodin can be administered to a patient at one time or over a series of treatments and may be administered to the patient at any time. Emodin may be administered as the sole treatment or in conjunction with other drugs or therapies useful in treating the pathology.

In one embodiment, a therapeutically effective amount of emodin can be in the range of about 1 ng/kg body weight/day to about 100 mg/kg body weight/day whether by one or more administrations. For example, emodin can be administered in an amount of from about 1 ng/kg body weight/day to about 1 µg/kg body weight/day, or from about 0.5 mg/kg body weight per day to about 50 mg/kg body weight/day, in some embodiments. In other particular embodiments, the amount of emodin administered can be from about, 0.0005 mg/day to about 1000 mg/day or from about 0.1 mg/day to about 500 mg/day in some embodiments. As expected, the dosage will be dependent on the condition, size, age and condition of the patient.

Emodin may be administered, as appropriate or indicated, in a single dose as a bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

In one embodiment, emodin can be administered to a subject in need thereof in conjunction with one or more additional therapeutically effective agents. For instance, emodin can be administered in conjunction with another anti-cancer agent, such as chemotherapy agent. Additional therapeutically effective agents can be administered as a component of the composition that includes the emodin or in a separate composition, as desired.

As used herein the term "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

Solutions or suspensions used for parenteral, intradermal, or subcutaneous application can include, without limitation, the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include, without limitation, physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent that delays absorption, for example, aluminum monostearate or gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, a pharmaceutical composition can be formulated for sustained or controlled release of emodin. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially, for example, from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form as used herein includes physically discrete units suited as unitary dosages for the subject to be treated; each unit may contain a predetermined quantity of active compound calculated to produce the desired therapeutic effect in association with the required pharmaceutical carrier. The specification for the dosage unit forms of the application is dictated by and directly dependent on the unique characteristics of the active compound and the particular therapeutic effect to be achieved, and the limitations inherent in the art of compounding such an active compound for the treatment of individuals.

The present invention may be better understood with reference to the Examples, set forth below.

Example 1

Peritoneal Macrophage Isolation and Culture—

Three milliliters of 4% Thioglycolate solution was injected intraperitoneally into 8-12 week old C57BL/6 mice. Three days later, macrophages were collected by lavaging the peritoneal cavity with PBS. The cells were then resuspended in DMEM containing 10% FBS. After 2 h, non-adherent cells were washed away with PBS and the macrophages were cultured overnight in serum free DMEM. The macrophages were then treated with DMEM containing IL4 (10 ng/ml, BioAbChem Inc. Ladson, S.C.) or LPS (100 ng/ml, Sigma-Aldrich) and IFN$\gamma$ (20 ng/ml, BioAbChem Inc) with or without emodin. Emodin was purchased from Nanjing Langze Medicine and Technology Co. Ltd (Nanjing, China) and dissolved in DMSO at a concentration of 10 mg/ml as a stock solution.

For macrophage memory experiments, macrophages were stimulated overnight with IL4, IFN$\gamma$, and/or emodin. Following, the cells were washed 3× with PBS and cultured for 2 or 5 days in DMEM with 2% FBS. The media were changed every 2 days. The cells were then re-stimulated with IL4 or LPS for 6 h.

Microarray Analysis—

Microarray analysis was carried out as described previously, with a few alterations. Macrophages were stimulated with IL4 for 6 h or LPS+IFN$\gamma$ for 24 h with or without emodin (50 $\mu$M). Samples were prepared in biological replicates of 4. Cells were lysed with Qiazol and RNA was extracted using Qiagen's miRNeasy kit. Agilent's 2100 Bioanalyzer was used to determine the quality and quantity of the RNA. All RNA samples had a RIN of 9.2 or higher. The RNA was amplified and labeled with Agilent's Low Input Quick Amp Labeling Kit (Agilent) according to the manufacturer's instructions. Labeled RNA was then purified using Qiagen's RNeasy Mini Kit (Qiagen, Valencia, Calif.) and dye incorporation and cRNA yield were assessed. Labeled samples were hybridized to Agilent Whole Mouse Genome Microarrays 8×60K (Agilent) using Agilent's Gene Expression Hybridization Kit (Agilent) according to the manufacturer's instructions. Microarray analysis was performed using an Agilent DNA Microarray Scanner System (Cat. # G2565CA).

A heatmap of genes from relevant pathways identified by Ingenuity pathway analysis was generated using R function heatmap. A principle component analysis was performed using all genes differentially expressed in at least one of the treatment groups using the R function prcomp.

Phagocytosis Assay—

Macrophages were seeded into a 96-well plate (2×10$^5$ cells/well) and were stimulated with IL4 or LPS+IFN$\gamma$ for 24 h with or without emodin. Phagocytotic activity was measured using a Vybrant Phagocytosis assay kit (Molecular Probes). The medium was removed and the cells were washed with PBS. The fluorescent BioParticle suspension was added to the cells and incubated up to 6 h. After the indicated time, the BioParticle suspension was removed, any extracellular fluorescence was quenched with trypan blue, and the intracellular fluorescence was detected using a Spectramax M5 microplate reader (Molecular Devices, Sunnyvale, Calif.).

Macrophage Migration Assay—

Macrophages were stimulated with IL4 or LPS+IFN$\gamma$ for 24 h with or without emodin. The media was then removed and the cells were washed with PBS. The cells were then resuspended in DMEM with scraping and 2×10$^5$ macrophages were seeded in triplicate into the top chamber of transwell inserts with 8 $\mu$m pores (Corning) and place in 24 well plates. Serum free DMEM with 20 ng/ml MCP1 was placed in the bottom of the wells. After 4 h, inserts were fixed in 4% paraformaldehyde for 20 min; the cells in upper inserts were swabbed using cotton buds, and the cells left on the membrane were stained with DAPI (1 $\mu$g/ml) for 1 min. The inserts were then cut out, mounted onto slides and imaged under a Nikon Eclipse NI-U fluorescence microscope (Nikon Inc. Melville, N.Y.) at 20× magnification (5 fields/insert). DAPI stained cells were quantified using Nikon NIS-Elements software.

NO Production Assay—

Macrophages were stimulated with LPS+IFN$\gamma$ for 24 h with various concentrations of emodin (0-50 $\mu$M). The culture media was then collected and the NO content was detected using a Nitrite/Nitrate colorimetric kit (Sigma-Aldrich) according to the manufacturer's instructions. The assay was read using a Spectramax M5 microplate reader (Molecular Devices, Sunnyvale, Calif.).

Western Blotting and Real Time PCR—

Following stimulation with IL4 or LPS+IFN$\gamma$ with or without emodin for varying periods, macrophages were lysed with cell signaling lysis buffer (Millipore) for whole cell lysates. Cytoplasmic and nuclear extracts were prepared using the Epiquik Nuclear Extraction kit (Epigentek, Farmingdale, N.Y.). Total protein was separated on 4-20% Tris-glycine pre-cast gels (Pierce) and transferred onto Nitrocellulose membranes (Bio-Rad Life Science, Hercules, Calif.). The membranes were then probed with HRP conjugated secondary antibodies, and signals were detected using Pierce ECL Western Blotting Substrate (Pierce).

For qPCR, macrophages were lysed with Qiazol and RNA was extracted using Zymo research Direct-zol RNA isolation kit. cDNA was then made from 1 microgram of RNA using iScript cDNA Synthesis Kit (Bio-Rad Life Science). Run conditions were 95° C. for 10 s, 58° C. for 15 s, 70° C. for 15 s. Samples were run in duplicate on a Bio-rad CFX Real Time thermocycler.

ChIP Assay—

Macrophages were stimulated with IL4 or LPS+IFNγ for 24 h with or without emodin. They were then fixed in 1% formaldehyde. Excess formaldehyde was quenched with glycine and the cells were collected in PBS by scraping. The cells were lysed (0.5% IGEPAL, 4 mM HEPES) and the nuclei were resuspended in nuclear lysis buffer (1% SDS, 10 mM EDTA, and 50 mM Tris, pH 8.1). The DNA was sheared by sonication using a Diagnode Bioruptor Pico for 15 cycles of 30 s on/30 s off. Then 10 µg chromatin was diluted 1:10 (0.01% SDS, 1.1% Triton X-100, 1.2 mM EDTA, 16.7 mM Tris-HCl, pH 8.1, 167 mM NaCl) and 2% of the input was removed from each sample and saved for analysis. Anti-H3K27m3 or anti-H3K27ac (Abcam) was added to each sample along with 20 µl of protein A+G magnetic beads (Millipore) and the samples were incubated overnight at 4° C. The beads were washed with low salt, high salt, LiCl, and TE wash buffers sequentially and the DNA was eluted off the beads with Proteinase K at 62° C. for 2 h (elution buffer: 200 mM NaCl, 1% SDS and 50 mM Tris). The DNA was then analyzed by real time PCR.

Statistical Analysis—

For microarray analysis, data was extracted from images with Feature Extractor Software version 10.7.3.1 (Agilent); background correction using detrending algorithms was performed. Subsequently, background-corrected data was uploaded into GeneSpring GX version 11.5.1 for analysis. In this process, data was log 2 transformed, quantile normalized and baseline transformed using the median of all samples. Data was filtered by flags in a way that 3 out of the 4 biological replicates had a "detected" flag in at least one of the three treatment groups. Differentially expressed genes were determined by analysis of the data using the Mann-Whitney unpaired statistics. A cutoff p-value of 0.05 and a fold change cutoff value of 2.0 were used to filter the data. Pathway analysis was performed using Ingenuity Pathway Analysis software.

For all other experiments, data were presented as mean±standard error of the mean (SEM). Statistical significance was calculated using Student's t test (two-group comparison) using the GraphPad Prism statistical program (GraphPad Software Inc., San Diego, Calif.). p≤0.05 was considered significant.

In order to comprehensively characterize emodin's effects on macrophage activation and to determine the mechanism of action, gene expression was analyzed using a whole genome microarray. Mouse peritoneal macrophages were stimulated with LPS/IFNγ or IL4 with/without emodin. It was found that LPS/IFNγ stimulation changed the expression of over 4,400 genes and IL4 changed the expression of over 700 genes (≥2 fold, p-value≤0.05) (GEO accession number GSE73311). FIG. 1A shows the effect of emodin treatment on the expression of genes that are significantly increased (upper panel) or decreased (lower panel) by LPS/IFNγ. Emodin treatment attenuated the LPS/IFNγ induced changes in about 31% of the LPS/IFNγ responsive genes. Similarly, emodin inhibited IL4 induced changes in almost 60% of IL4 responsive genes (FIG. 1B). These results indicate that emodin significantly inhibited the transcription programs induced by both M1 and M2 stimuli.

LPS/IFNγ and IL4 induce macrophage activation through competing signaling pathways (STAT1 vs. STATE, IRF4 vs. IRF5), resulting in little overlap between the transcriptional programs induced by LPS/IFNγ or IL4. The majority of genes changed by LPS/IFNγ treatment and almost half of the genes changed by IL4 were unchanged in the other treatment group (FIG. 1C, upper). The expression of almost 6,500 genes was changed by emodin in at least one of the conditions; among them only 1,575 were changed in both groups (FIG. 1C, lower). Therefore, emodin treatment predominately affected different transcriptional programs under the two different conditions. These results were confirmed with a principle component analysis (PCA) of the genes that were significantly changed in at least one of the treatment groups (~10,000 genes) (FIG. 1D). The samples within each group cluster near each other with LPS/IFNγ treated cells clustering much further from naïve cells than IL4 treated cells, indicating that M1 activation involves much greater transcriptional changes than M2. Similarly, there was significant distance between the two emodin treatment groups, indicating that emodin treatment differentially affected the expression of transcriptional programs under the different conditions.

Cell signaling pathways targeted by emodin were investigated by performing a canonical signaling pathway analysis using Ingenuity IPA. The genes influenced by emodin treatment were enriched for genes associated with immune cell signaling, inflammation, cell adhesion, and metabolism. FIG. 2 shows a list of pathways with the highest significance. Several pathways were targeted by emodin under both conditions, including: communication between immune cells, granulocyte adhesion, NFκB signaling, and Toll-like receptor signaling. However, most of the pathways targeted by emodin were different under the different conditions. The genes changed by emodin under LPS/IFNγ stimulation were enriched for M1 associated pathways: antigen presentation, IL1 signaling, and iNOS signaling; whereas, the genes changed by emodin under IL4 stimulation were enriched for M2 associated pathways: IL4, JAK/STAT, TGFβ, and VEGF signaling.

Emodin significantly attenuated the LPS/IFNγ induced changes in a large number of genes including canonical M1 associated genes: proinflammatory cytokines IL1β, TNFα, and IL6 (13.64, 2.01, and 3.25 fold reduction, respectively); proteases MMP2/9 (11.86 and 28.87 fold reduction, respectively); and antigen presentation genes CD86 and H2-Oa/b (7.74, 3.85, and 6.42 fold reduction, respectively) (Table 1). Similarly, emodin inhibited the IL4 induced expression of canonical M2 genes Arg1, Mrc1, and Ch3I3 (7.69, 2.29, and 4.24 fold reduction, respectively); and transcription factors SOCS1 and IRF4 (22.9 and 97.43 fold reduction, respectively) which have both shown to be necessary for M2 activation (8,37,38) (Table 2). Emodin also increased the expression of CDKN1A (p21) which has been shown to inhibit macrophage proliferation and activation.

TABLE 1

| Gene Symbol | LPS/IFN vs. Control | Em + LPS vs. LPS/IFN |
|---|---|---|
| H2-Ob | 6.30 | −6.42 |
| IL1RL1 | 9.66 | −10.78 |
| MMP2 | 7.57 | −11.86 |
| CD86 | 17.11 | −7.74 |
| SELL | 15.77 | −10.45 |
| IFIT1 | 25.61 | −11.94 |
| MYH3 | 3.48 | −7.76 |
| MMP9 | 7.65 | −28.87 |
| IRF5 | 1.30 | −2.11 |
| CCL2 | 96.07 | −12.06 |
| RASGRP1 | 75.14 | −8.52 |

TABLE 1-continued

| Gene Symbol | LPS/IFN vs. Control | Em + LPS vs. LPS/IFN |
|---|---|---|
| FPR2 | 401.98 | −33.81 |
| IL1B | 358.98 | −13.64 |
| CXCL10 | 770.25 | −10.31 |
| CCL5 | 238.95 | −5.41 |
| TNF | 79.29 | −2.01 |
| IL12A | 77.45 | −4.93 |
| SOCS1 | 110.62 | −5.34 |
| IRF7 | 82.09 | −4.20 |
| H2-Oa | 32.62 | −3.85 |
| CXCL2 | 33.32 | −2.47 |
| CXCL3 | 32.80 | −2.47 |
| IL12B | 838.87 | 2.47 |
| IL6 | 1814.11 | −3.25 |
| NOS2 | 3043.88 | −3.77 |
| PTGS2 | 3745.38 | −3.99 |
| Mrc1 | −8.48 | 8.72 |
| TLR4 | −1.72 | −4.71 |

TABLE 2

| Gene Symbol | LPS/IFN vs. Control | Em + LPS vs. LPS/IFN |
|---|---|---|
| CDKN1A | 1.08 | 29.78 |
| CXCL2 | −2.24 | 60.63 |
| CCL28 | 2.45 | 2.27 |
| CXCL10 | −4.60 | 15.05 |
| CXCR1 | −3.45 | 12.40 |
| TNF | −2.16 | 2.69 |
| PLA2G5 | 4.15 | 4.26 |
| MMP13 | 8.35 | 3.68 |
| PTGS2 | 4.85 | 2.56 |
| Arg1 | 136.43 | −7.69 |
| CISH | 474.12 | −7.11 |
| SOCS1 | 29.55 | −22.90 |
| FLT1 | 22.64 | −27.09 |
| RBP4 | 34.94 | −15.56 |
| CCL11 | 14.11 | −11.31 |
| IL19 | 20.98 | −20.01 |
| IRF4 | 27.25 | −97.43 |
| ITGB8 | 4.23 | −4.32 |
| Mrc1 | 4.28 | −2.29 |
| FCGR2B | 5.32 | −2.15 |
| SOCS2 | 8.70 | −5.47 |
| CDH1 | 10.19 | −5.72 |
| IL6 | 7.70 | −5.30 |
| CCL7 | 20.39 | −4.16 |
| CCL12 | 20.08 | 2.30 |
| Ccl2 | 3.51 | −4.26 |
| IL1R1 | 3.25 | −2.15 |
| Chi3l3 | 6.97 | −4.24 |
| IRF5 | −1.06 | −2.58 |

Interestingly, it was also found that emodin treatment had inverse effects on a subset of 86 genes under the two different stimuli. For examples, emodin increased the expression of some proinflammatory genes including TNFα, CXCL2, and CXCL10 (2.7, 60.6, and 15.5 fold, respectively) under IL4 stimulation while significantly decreasing them (−2.47, −10.31, and −2.01 fold, respectively) under LPS/IFNγ stimulation (Table 1, 2). Similarly, emodin increased the expression of M2 genes YM1 and Mrc1 under LPS/IFNγ stimulation (2.04 and 8.72 fold, respectively), while reducing them in IL4-stimulated cells. These results show emodin's ability to tune macrophage phenotype back towards the center between the extremes of the M1 or M2 activation states.

Figure 3A:
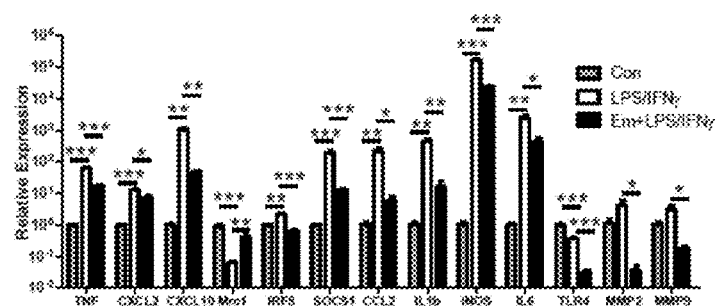
FIG. 3A graphically illustrates emodin inhibition of expression of M1 genes. qPCR was performed to verify the microarray results for select M1 genes. Bars represent the mean±S.E. For each treatment, n=4.
Figure 3B:
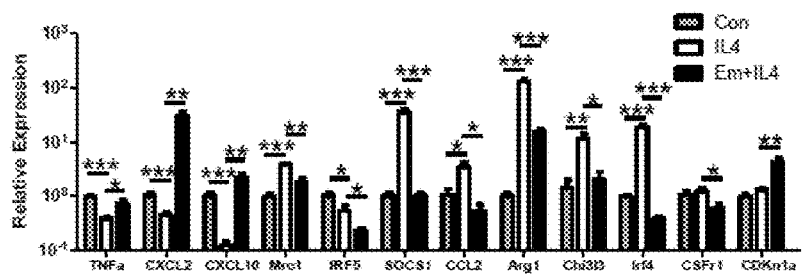
FIG. 3B graphically illustrates emodin inhibition of expression of M2 genes. qPCR was performed to verify the microarray results for select M2 genes. Bars represent the mean±S.E. For each treatment, n=4.
Figure 3C:
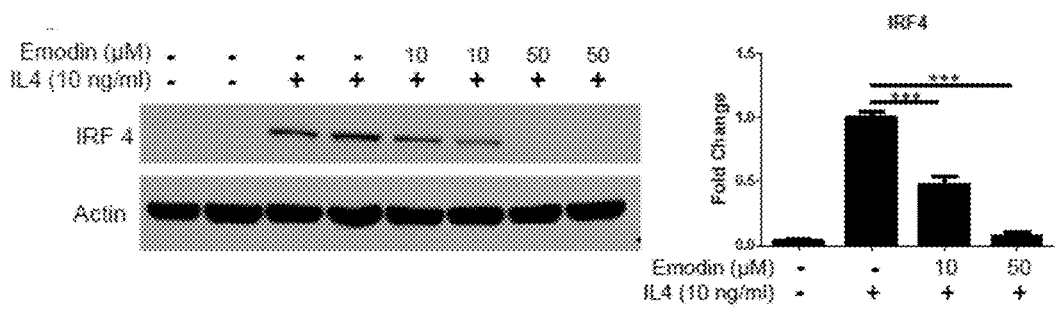
FIG. 3C illustrates the results of macrophage stimulation with IL4 with or without emodin (0-50 μM) for 6 h. The cells were lysed and IRF4 protein levels were detected by western blotting. Results are shown as the means±S.E. for two independent experiments (n=4) $*p<0.05$, $p<0.01$, $*p<0.001$.

The expression of several important genes for macrophage activation was confirmed by qPCR (FIG. 3A, FIG. 3B). Emodin inversely regulated M1 genes TNFα, CXCL2 and CXCL10, and M2 gene Mrc1, in the two settings. Interestingly, emodin inhibited the expression of transcription factors IRF5 and SOCS1, and chemoattractant CCL2 under both IL4 and LPS stimulation. In agreement with the microarray data, emodin inhibited the expression of many pro-inflammatory mediators including IL1β, iNOS, and IL6 as well as proteases MMP2 and 9 under LPS/IFNγ stimulation, and inhibited M2 genes Arg1 and Chi3I3 under IL4 stimulation. Emodin also inhibited the expression of receptors TLR4 and CSFr1 under LPS/IFNγ or IL4 stimulation, respectively, which could further inhibit macrophages from detecting activation signals in the environment. IRF4, a major regulator of M2 macrophage activation, was the most down regulated gene by emodin under IL4 stimulation in the microarray dataset. The production of IRF4 protein was examined and it was found that emodin dose dependently inhibited IRF4 production (FIG. 3C).

Figure 4A:
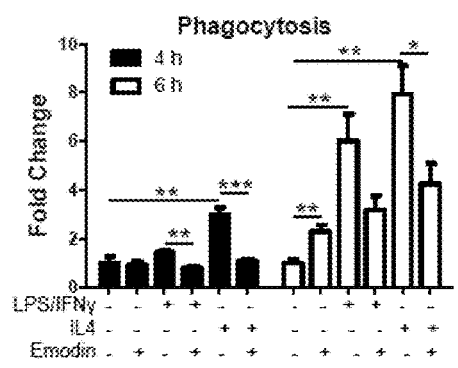
FIG. 4A graphically illustrates results following stimulation of mouse peritoneal macrophages with LPS (100 ng/ml) and IFNγ (20 ng/ml) or IL4 (10 ng/ml) with or without emodin (50 μM) for 24 h. The macrophages were washed and the cells were incubated with FITC-labeled E. coli bioparticles for 4-6 h. Fluorescence was detected with a microplate reader as an indicator of phagocytosis. Results are shown as the mean±SE (n=4).
Figure 4B:
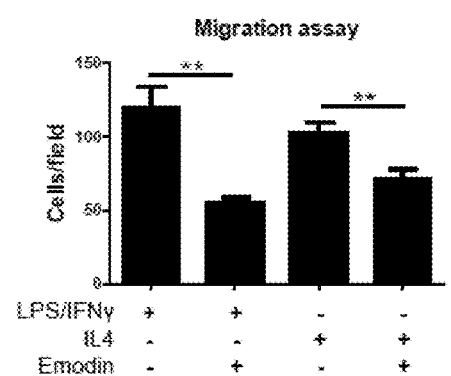
FIG. 4B graphically illustrates results following stimulation of mouse peritoneal macrophages with LPS (100 ng/ml) and IFNγ (20 ng/ml) or IL4 (10 ng/ml) with or without emodin (50 μM) for 24 h. The macrophages were seeded into the top chamber of a transwell insert in DMEM, and DMEM with MCP1 (20 ng/ml) was placed in the bottom of the well. After 4 h, cells were fixed, stained with Dapi, and imaged with 5 fields of view at 20× magnification per membrane. Results are shown as the mean±SE for two independent experiments (n=3).

The effects of emodin on the functions of macrophages was examined, which were predicted to be inhibited by emodin in one or both of the groups based on pathway analysis of the microarray results. The phagocytic ability of activated macrophages was examined. Macrophages were pretreated with LPS/IFNγ or IL4 with or without emodin for 24 h; then the cells were incubated with Fitc-labeled *E. Coli* bioparticles. Emodin treatment alone was able to increase phagocytic activity of naïve cells at the 6 h time point; however, emodin decreased phagocytosis in either IL4 or LPS/IFNγ treated cells. Both IL4 and LPS/IFNγ stimulated macrophages showed time dependent increases in bioparticle uptake (6-8 fold increase at 6 h). However, emodin significantly inhibited particle uptake under both conditions (by almost 2 fold) (FIG. 4A). Next, macrophages were stimulated with LPS/IFNγ or IL4 with or without emodin then their migration potential was detected. Macrophages were seeded into the top chamber of transwell inserts and media containing MCP1 (20 ng/ml) was placed in the bottom. Emodin significantly reduced macrophage migration under both conditions (FIG. 4B).

Figure 4C:
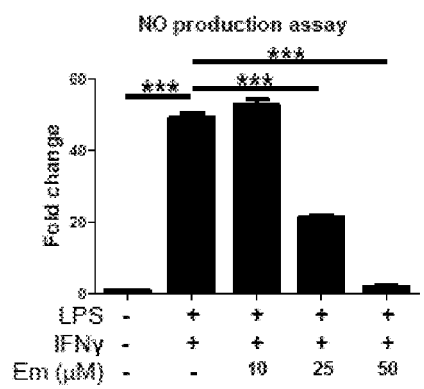
FIG. 4C graphically illustrates results following stimulation of mouse peritoneal macrophages with LPS (100 ng/ml) and IFNγ (20 ng/ml) with or without emodin at various concentrations for 24 h. The macrophages were incubated with LPS/IFNγ with emodin at various concentrations. After 24 h the media were collected and NO content was detected. Results are shown as the mean±SE (n=4).$*p<0.05$, $p<0.01$, $*p<0.001$.

Emodin's ability to inhibit M1 activation was verified by detecting NO production. Macrophage production of NO was measured in the culture media following stimulation with LPS/IFNγ for 24 h. The result showed that emodin dose dependently inhibited NO production (FIG. 4C).

Figures 5A, 5B:
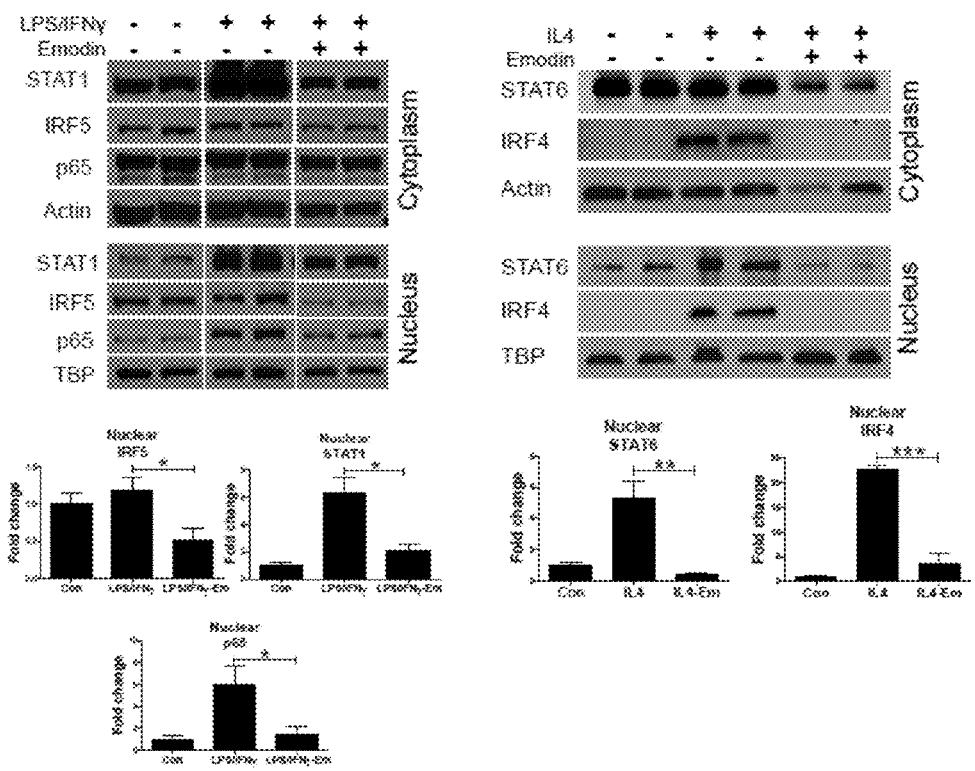
FIG. 5A presents results of emodin inhibition of LPS/IFNγ and resulting induced activation of various signaling pathways. Macrophages were stimulated with LPS (100 ng/ml) and IFNγ (20 ng/ml) with or without emodin (50 μM) for 24 h. Cells were lysed and cytoplasmic and nuclear fractions were collected. Transcription factors were then detected in both fractions using western blotting. Bottom panels, quantification of blots of nuclear fractions normalized to loading control TBP. Results are shown as the mean±SE for two independent experiments (n=4). $*p<0.05$, $p<0.01$, $*p<0.001$.
FIG. 5B presents results of emodin inhibition of IL4 and resulting induced activation of various signaling pathways. Macrophages were stimulated with IL4 (10 ng/ml) with or without emodin (50 μM) for 24 h. Cells were lysed and cytoplasmic and nuclear fractions were collected. Transcription factors were then detected in both fractions using western blotting. Bottom panels present the quantification of blots of nuclear fractions normalized to loading control TBP. Results are shown as the mean±SE for two independent experiments (n=4). $*p<0.05$, $p<0.01$, $*p<0.001$.

The cell signaling pathways targeted by emodin under the different conditions were identified. Nuclear translocation of transcription factors was investigated by western blotting using cytoplasmic and nuclear cell fractions. As shown, emodin was able to drastically inhibit NFκB p65 nuclear translocation in response to LPS/IFNγ stimulation (FIG. 5A) and STAT6 nuclear translocation in response to IL4 stimulation (FIG. 5B). Emodin also inhibited nuclear IRF4 (FIG. 5B), in agreement with the gene expression data. Further, it was found that emodin inhibited STAT1 and IRF5 nuclear translocation (FIG. 5A). These results indicate that emodin is able to inhibit the key signaling pathways necessary for macrophage polarization.

The global expression of histone modifications was examined using western blotting and it was found that emodin had no effect on the global expression of either H3K27m3 or H3K27ac (FIG. 6A). Gene specific changes in histone modifications were then examined using ChIP assays. It was found that emodin attenuated LPS/IFNγ-induced decrease of H3K27m3 in the promoter of iNOS, TNFα and IL6 genes, and reversed IL4-induced decrease of H3K27m3 in the promoter of IRF4, Arg1 and YM1 genes. Emodin also suppressed LPS/IFNγ-induced increase of H3K27ac in the promoters of iNOS, TNFα and IL6 genes, and IL4-induced increase of H3K27ac in the promoter of IRF4 and YM1 genes (FIG. 6B and FIG. 6C). These data show that emodin epigenetically regulated macrophage activation. Further, unlike emodin's effects on signaling pathways, emodin's effects on histone modification are not stimuli dependent, but gene specific.

Figure 7A:
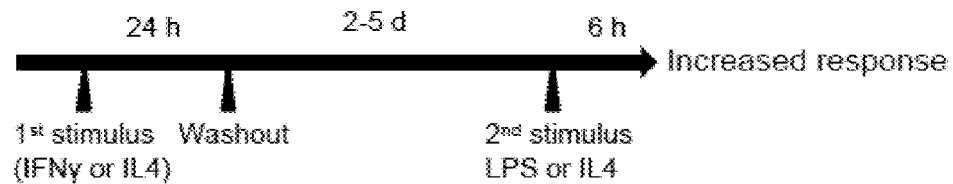
FIG. 7A presents a diagram of macrophage treatments for testing the effects of emodin on macrophage memory. Macrophages were incubated with IFNγ (20 ng/ml) or IL4 (10 ng/ml) with or without emodin (50 μM) for 24 h. The cells were washed and incubated for 2 d or 5 d (washout periods), and then stimulated with either IL4 or LPS for 6 h.
Figure 7B:
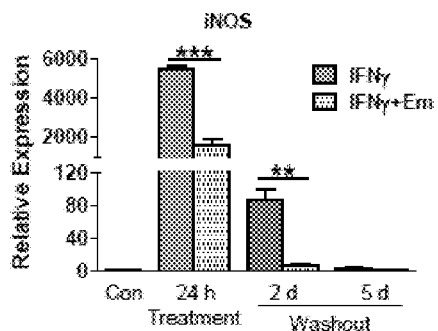
FIG. 7B presents gene expression analysis with qPCR after the first treatment with IFNγ for 24 h and after 2 d or 5 d washout period, compared with baseline control (set as 1).
Figure 7C:
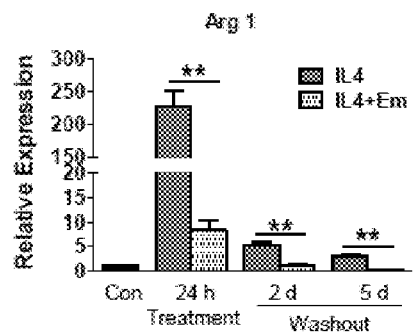
FIG. 7C presents gene expression analysis with qPCR after the first treatment with IL4 for 24 h and after 2 d or 5 d washout period, compared with baseline control (set as 1).
Figure 7D:
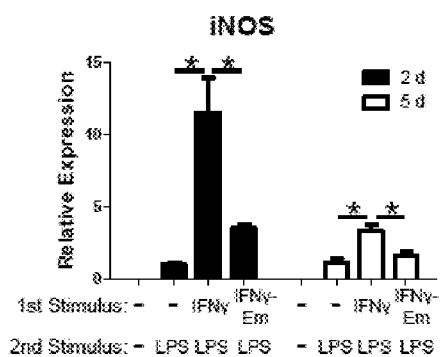
FIG. 7D presents gene expression analysis after a first treatment with IFNγ and the cells were then re-stimulated with LPS for 6 h following 2 d or 5 d washout period.
Figure 7E:
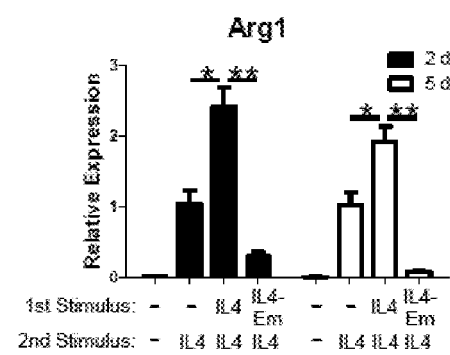
FIG. 7E presents gene expression analysis after a first treatment with IL4 and the cells then re-stimulated with IL4 for 6 h following 2 d or 5 d washout period.
Figure 7F:
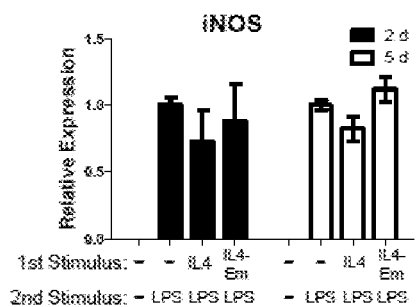
FIG. 7F presents results of crossover experiments, in which macrophages were first treated with IL4 for 24 h, and after 2 d or 5 d washout period, the cells were further treated with LPS for 6 h, and gene expression was analyzed.
Figure 7G:
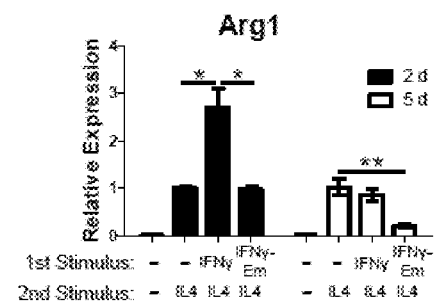
FIG. 7G presents results of crossover experiments, in which macrophages were first treated with IFNγ for 24 h, and after 2 d or 5 d washout period, the cells were further treated with IL4 for 6 h, and gene expression was analyzed. For all of FIGS. 7B-7G, results are shown as the mean±SE for two independent experiments (n=3).
Figure 7H:
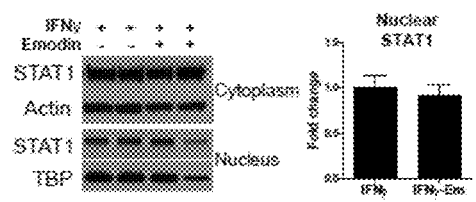
FIG. 7H presents results following lyse of macrophages after the 5 d rest period followed by collection and analysis of cytoplasmic and nuclear protein fractions via western blotting. Results are shown as the mean±SE for two independent experiments (n=4). $*p \leq 0.05$; $p \leq 0.01$, $*p<0.001$.
Figure 7I:
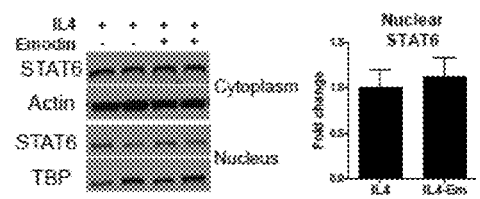
FIG. 7I presents results following lyse of macrophages after the 5 d rest period followed by collection and analysis of cytoplasmic and nuclear protein fractions via western blotting. Results are shown as the mean±SE for two independent experiments (n=4). $*p \leq 0.05$; $p \leq 0.01$, $*p<0.001$.

The effects of emodin on macrophage memory were investigated. Macrophages were stimulated with IFNγ or IL4 for 24 h with or without emodin. Then the cells were cultured in fresh media for 2-5 d before being stimulated again with LPS or IL4 for 6 h without emodin (FIG. 7A). The expression of iNOS returned to baseline levels by 5 d post stimulation with IFNγ, while the expression of Arg1 was still elevated 5 d post IL4 treatment (FIG. 7B, FIG. 7C). IFNγ treatment significantly increased macrophage's response to a subsequent LPS treatment, with an 11.5 and 3.3 fold increase in iNOS expression after 2 d and 5 d washout post the first IFNγ treatment, respectively, compared with the cells without IFNγ treatment (FIG. 7D). Similarly, after 2 d and 5 d washout after the first treatment with IL4, macrophages responded significantly more robustly to a second IL4 treatment, with 2.4 and 1.9 fold increases in Arg1 expression, respectively (FIG. 7E). However, when the cells were first concomitantly treated with emodin with IFNγ or IL4, their responses to the second LPS or IL-4 treatment were significantly diminished (FIG. 7D, FIG. 7E). Interestingly, in a crossover experiment, IL4 pre-treatment showed no effects on macrophage response to LPS 2 or 4 days after the pre-treatment and co-pretreatment with emodin did not have any effects (FIG. 7F); however, pretreatment with IFNγ increased macrophage response to IL4 2 days after IFNγ treatment, but this effect was diminished within 5 days post IFNγ treatment, and emodin co-pretreatment decreased the response to the secondary IL-4 stimulation (FIG. 7G). After 5 days of wash-out period, there was no significant difference in the nuclear STAT1 or STAT6 in IFNγ or IL4 pretreated cells, respectively, regardless if the cells were also treated with emodin (FIG. 7H, FIG. 7I). The lack of differences in the STAT1 and STAT6 signaling pathway prior to re-stimulation indicates that emodin may regulate macrophage memory through epigenetic modification of the key genes in macrophage activation.

Figure 8A:
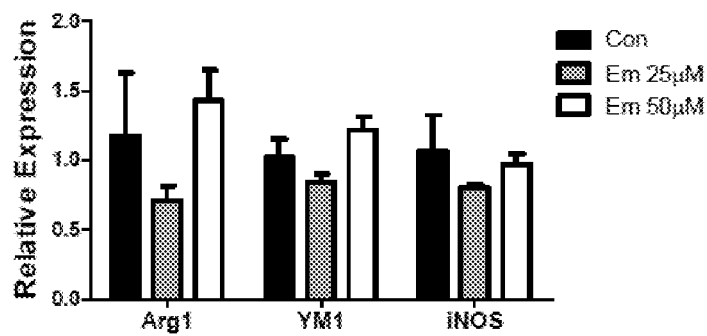
FIG. 8A graphically illustrates gene expression following incubation of macrophages with various concentrations of emodin (0-50 μM) for 24 h—gene expression was analyzed using qPCR.

To examine if emodin had any efforts on naïve macrophages and if emodin pretreatment alone may affect the subsequent response to polarization signals, mouse peritoneal macrophages were first treated with emodin at 25 or 50 μM for 24 h, and no effects of emodin on the expression of macrophage polarization markers iNOS, Arg1 and YM1 were found (FIG. 8A). Macrophages were then treated with 50 μM emodin alone for 24 h; and after a 2-d washout period, were stimulated with LPS or IL4 for 6 h. Emodin pretreatment had no effect on macrophage response to LPS, but significantly reduced their response to IL4 (FIG. 8B). These data further suggest that while emodin may not influence the basal phenotype of macrophages, it can change the respond to subsequent polarization signals, particularly M2 polarization signals, possibly by altering the epigenetic landscape of the cells.

Example 2

Emodin was purchased from Nanjing Langze Medicine and Technology Co. Ltd (Nanjing, China) and verified by NMR spectroscopy and mass spectrometry.

4T1 cells were obtained from the American Type Culture Collection (ATCC), and EO771 cells were developed from an ER+ spontaneous mammary adenocarcinoma. The cells were maintained in culture according to standard practice.

For tumor conditioned medium (TCM) collection, cells were grown until they were 80-90% confluent. Following, the medium was replaced with serum free (SF) DMEM and the cells were cultured for 48 h. The medium was then collected and passed through a 0.45 μm filter (Millipore Corp., Bedford, Mass.). The medium was concentrated 10 times using centrifuge filters with a 3,000 MW cutoff (Millipore). Before use the concentrated conditioned medium was diluted 1:2 with fresh SF DMEM.

Tumor cells ($2 \times 10^4$ EO771 or 4T1 cells) were seeded into 96 well culture plates in DMEM with 10% FBS. The cells were incubated overnight at 37° C. The medium was then removed, and the cells were washed with phosphate-buffered saline (PBS). DMEM containing varying concentrations of emodin (0-100 μM) was then added to the cells in quadruplicate. Vehicle control contained an equal volume of DMSO. Plates of cells were then incubated for 24-48 h. After an indicated period, the viability of the cells was determined using a Lactate Dehydrogenase (LDH) Cytotoxicity Detection Kit (Clontech Mountain View, Calif.) according to the manufacturer's instructions. Briefly, the supernatant was removed from each well on the plate and placed in a new well on the same plate. An equal volume of cell lysis buffer (2% triton in DMEM) was then added to each well containing the cancer cells, and the cells were incubated at room temperature for 15 min. The reaction mixture was then added to each well (cell lysate plus supernatant) and incubated for 5 min before the stop solution was added. The absorbance was measured at 490 nm on a Spectra Max M5 Microplate Reader (Molecular Devices, Sunnyvale, Calif.). The percent viability was then calculated as the ratio of LDH in the cell lysate to the total amount of LDH in the lysate plus the supernatant. The viability of each group was compared to the control.

C57BL/6 and BALB/c mice (8-12 weeks, female) were purchased from Jackson Labs (Bar Harbor, Me.). They were housed at the University of South Carolina Animal Research Facility, and all procedures were approved by the Institutional Animal Care and Use Committee. EO771 or 4T1 cells ($2 \times 10^5$) in 20 μL of PBS were injected into the $4^{th}$ pair of mammary glands on C57BL/6 mice or BALB/C, respectively, on Day 0. Starting on Day 1, emodin (40 mg/kg) or vehicle (2% DMSO) was injected intraperitoneally in 1 ml PBS once daily. The tumor size was measured using a caliper every 2-4 days, and the tumor volume was calculated using a formula: V ($mm^3$)=L (major axis)$\times W^2$ (minor axis)/2. Mice were sacrificed at various time points.

The tumor draining lymph nodes and tumors were collected, and cell populations were analyzed using flow cytometry. Briefly, cells were stained with anti-CD3 FITC, anti-CD4 APC or anti-CD8 APC, and anti-CD25 PE (Biolegend) in PBS containing 2% FBS for 30 min at 4° C. Samples were washed twice with staining buffer and analyzed by flow cytometry using a BD FACS flow cytometer and CXP software version 2.2 (BD Biosciences, San Jose, Calif.). Data were collected for 20,000 live events per sample.

For Ki67 staining, 4T1 and EO771 tumor cells were seeded into 6 well plates and cultured in SF DMEM overnight. They were then treated with various concentrations of emodin (0-50 μM) for 24 h. The cells were resuspended with trypsin plus EDTA and fixed with 1% paraformaldehyde. The cells were then permeabilized with 0.25% Triton X-100 and stained with anti-Ki67 PE (Abcam). The cells were washed and incubated with goat anti-rabbit Alexa 488 (Invitrogen, Eugene, Oreg.). After washing, the samples were analyzed by flow cytometry using a BD FACS flow cytometer and CXP software version 2.2. Data were collected for 10,000 live events per sample.

At sacrifice, tumors were embedded in OCT. They were then cut into 8 μm thick frozen sections and placed on slides. For immunohistochemistry staining, the sections were fixed with 4% paraformaldehyde for 10 min, and then blocked with 0.01 M glycine containing 0.1% Triton x-100. Next, the sections were blocked with 5% BSA. They were then incubated in primary antibody overnight at 4° C.: anti-F4/80 (1:50, Biolegend), anti-pSTAT6 (1:50, Cell Signaling), or anti-C/EBPβ (1:50, Santa Cruz). The sections were washed with PBS and then incubated with secondary antibodies for 1 h at room temperature. The sections were then stained with DAPI (1 μg/mL) and coverslipped with DABCO. Slides were imaged using a Zeiss LSM 510 Confocal microscope (Zeiss, Peabody, Mass.). For quantitative analysis, the number of positive cells was manually counted in six random fields of view per section. CD31 staining was performed according to standard methodology. Slides were imaged on a Nikon ECLIPSE E600 microscope (Nikon, Melville, N.Y.) at 200× magnification (10 fields per section). The integrated optical density (IOD) of CD31 was quantified using Image-Pro Plus software.

Macrophages or T cells were isolated from 4T1 tumors from mice sacrificed at 6 weeks post implantation or from EO771 tumors 5 weeks post implantation, using EasySep™ Mouse PE Positive Selection Kit (Stem Cell Technologies, Vancouver, BC). For cell isolation, $1\times10^7$-$1\times10^8$ cells were incubated with 20 μL PE conjugated anti-F4/80 (Biolegend) for macrophages or 20 μL PE conjugated anti-CD3 for T cells and 50 μL microbeads. The T cells and macrophages were lysed in Qiazol and used for RT-PCR analysis. For ChIP assays, 5-10×$10^6$ macrophages were fixed in 1% formaldehyde.

Mice were injected with 3 mL of 4% thioglycollate solution. After 3 d, macrophages were collected by peritoneal lavage with PBS. The cells were resuspended in DMEM with 10% FBS and cultured for 2 h. The non-adherent cells were then washed away and the remaining cells were cultured overnight in SF DMEM. The cells were then treated with TCM with or without emodin.

For qPCR, cells were lysed with Qiazol, and RNA was extracted using Zymo research Direct-zol RNA isolation kit. cDNA was then made from 1 μg of RNA using iScript cDNA Synthesis Kit (Bio-Rad Life Science, Hercules, Calif.). Run conditions were 95° C. for 10 s, 58° C. for 15 s, 70° C. for 15 s. Samples were run in duplicate on a Bio-rad CFX Real Time thermocycler.

Macrophages were fixed in 1% formaldehyde. Excess formaldehyde was quenched with glycine, and the cells were collected in PBS by scraping. The cells were lysed (0.5% IGEPAL, 4 mM HEPES), and the nuclei were resuspended in nuclear lysis buffer (1% SDS, 10 mM EDTA, and 50 mM Tris, pH 8.1). The DNA was sheared by sonication using a Diagnode Bioruptor Pico (Diagenode, Denville, N.J.) for 25 cycles of 30 s on/30 s off. Then 8 μg chromatin was diluted 1:10 (0.01% SDS, 1.1% Triton X-100, 1.2 mM EDTA, 16.7 mM Tris-HCl, pH 8.1, 167 mM NaCl), and 2% of the input was removed from each sample and saved for analysis. Anti-H3K27m3 (Abcam) was added to each sample along with 20 μL of protein A+G magnetic beads (Millipore), and the samples were incubated overnight at 4° C. The beads were washed with low salt, high salt, LiCl, and TE wash buffers sequentially, and the DNA was eluted off the beads with Proteinase K at 62° C. for 2 h (elution buffer: 200 mM NaCl, 1% SDS and 50 mM Tris). The DNA was then analyzed by qPCR.

In order to detect genome wide levels of histone H3 modifications, histones were isolated from macrophages treated with TCM with or without emodin for 24 h using EpiQuik total histone extraction kits (Epigentek, Farmingdale, N.Y.) according to the manufacturer's instructions. Histones (100 ng) were then analyzed using an EpiQuik Histone H3 modification kits (EpiGentek) according to the manufacturer's instructions.

Peritoneal macrophages were seeded into 10 cm plates and treated with EO771 conditioned medium with or without emodin for 24 h. The cells were then washed with PBS and resuspended. T cells were isolated from the spleens of C57BL/6 mice using EasySep T cell isolation kit (Stem Cell Technologies) according to the manufacturer's instructions. For the proliferation assay, T cells were labeled with CSFE and then mixed with macrophages and CD3/CD28 DYNA beads in a 1:1:1 ratio and added to 12 well plates in triplicate. For the activation assay, the T cells were collected after 24 h and stained with anti-CD3, anti-CD4, and anti-CD69 for 30 min at 4° C. The cells were then analyzed on a BD FACS flow cytometer. For the proliferation assay, T cells were collected after 72 h and stained with anti-CD3 and anti-CD4. The cells were analyzed for CSFE depletion on a Beckman Coulter FC500.

EO771 or 4T1 cells were treated with 0-50 μM emodin for 24 h. The cells were then washed multiple times with PBS, further cultured, and TCM was collected. The TCM was placed in the bottom chamber of transwell inserts, and $2\times10^5$ macrophages were seeded into the top chamber in SF DMEM. The cells were incubated at 37° C. with 5% $CO_2$ for 4 h. The membranes were then fixed with 4% paraformaldehyde for 10 min. The cells were removed from the top chamber using cotton swabs, and the cells on the bottom chamber were stained with DAPI (1 μg/mL). The inserts were then cut out, mounted onto slides, and imaged under a Nikon Eclipse E-600 fluorescence microscope (Nikon Inc. Melville, N.Y.) at 20× magnification (5 fields/insert). DAPI stained cells were quantified using ImagePro Plus software.

Tumor cell monolayers (80-90% confluent) and macrophages were treated with emodin (0-25 μM) overnight. The cells were then washed multiple times with PBS, and fresh SF DMEM was added. Macrophages were resuspended with scraping and $5\times10^5$ cells were seeded onto the tumor cell monolayers. After 1 h the non-adherent cells were washed away, and the adherent cells were resuspended with Trypsin and mild scraping. The total number of cells was counted, and cells were stained with anti-F4/80 FITC (Biolegend). The cells were analyzed on a Beckman Coulter FC500.

For all experiments, data were presented as mean±standard error of the mean (SEM). For two-group comparison, statistical significance was calculated by 2-tailed Student's t test. For multiple group comparison, one-way ANOVA was used followed by Tukey multiple comparison test. All statistical analyses were performed using the GraphPad Prism statistical program (GraphPad Software Inc., San Diego, Calif.). P 0.05 was considered significant.

Breast cancer EO771 and 4T1 cells were injected into the mammary glands of C57Bl/6 or Balb/c mice, respectively, and emodin treatment (40 mg/kg IP once daily) began 1 day after tumor cell injection. Emodin caused a significant inhibition of primary tumor growth (FIG. 9A, FIG. 9C) and tumor weight (FIG. 9B, FIG. 9D) at the endpoints in both EO771 and 4T1 models.

Figure 10A:
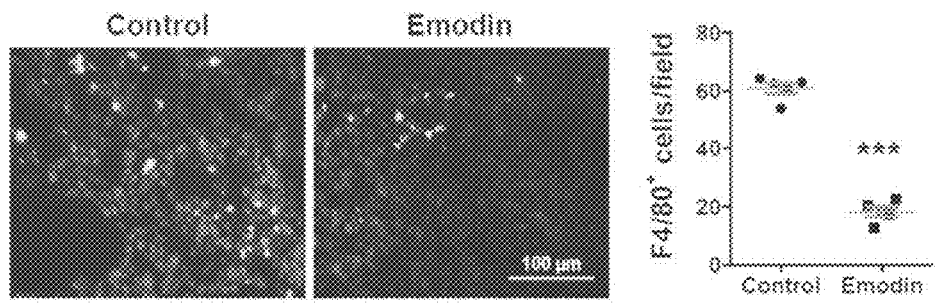
FIG. 10A illustrates EO771 tumors embedded in OCT (n=5). Tumors were cut into 8-μm sections and stained for F4/80. Sections were imaged (200×, 10 fields per section), and the number of positive cells was manually counted (graph). Results are shown as mean±S.E.
Figure 10B:
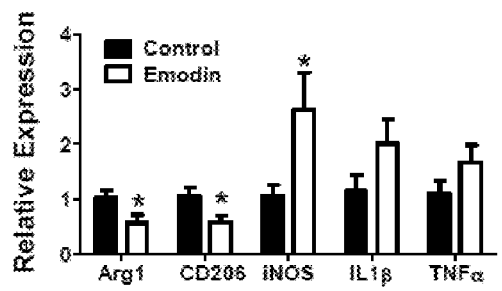
FIG. 10B presents determination of gene expression as detected using RT-qPCR. F4/80$^+$ cells were isolated from the EO771 tumors of C57BL/6 mice (n=5).

Macrophage infiltration and phenotype in EO771 tumor bearing mice at the experimental endpoint was investigated. Immunohistochemical analysis revealed that emodin reduced the number of tumor infiltrating macrophages by 70% (FIG. 10A). F4/80+ cells were extracted from the tumors using magnetic beads and qPCR was used to examine the expression levels of M1 or M2 macrophage markers. qPCR showed that TAMs in the emodin-treated mice had significantly lower M2 marker (Arg1 and CD206) expression but significantly higher M1 marker (iNOS) expression and also had higher expression levels of inflammatory cytokines IL1β and TNFα, although without statistical significance (FIG. 10B).

Figure 10C:
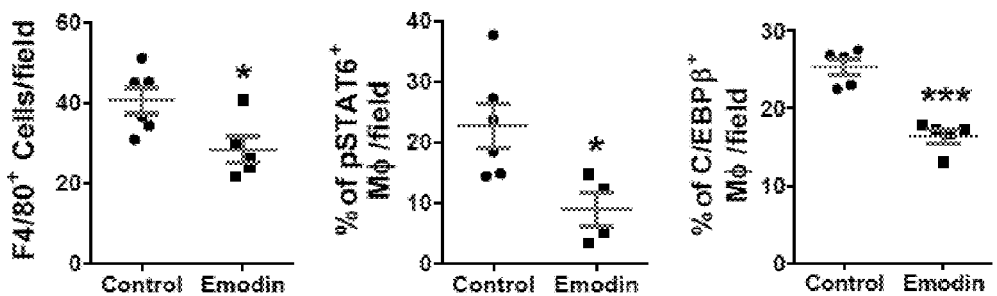
FIG. 10C illustrates results of tumor examination for F4/80 and pSTAT6 or C/EBPβ. 4T1 tumors from Balb/c mice were collected 26 days post injection and embedded in OCT (n=6 for control, n=5 for emodin group). Tumors were cut into 8-μm sections and stained. Sections were imaged (200×, 5 fields per section), and the number of positive cells was manually counted. Results are shown as mean±S.E.

To exclude the possibility that reduced total TAMs and M2 marker expression in emodin-treated breast cancer mice was the result of halted tumor growth instead of it being the cause, emodin's effects on macrophages in tumors was investigated at the time point when there was no difference in the size of the tumors between the two groups. Emodin significantly reduced the number of macrophages in 4T1 tumors 26 days post implantation while the tumor size was not different between the two groups at this time point; moreover, emodin significantly reduced the fraction of macrophages positive for transcription factors pSTAT6 and C/EBPβ (FIG. 10C), indicating that emodin indeed directly inhibited macrophage infiltration and M2 polarization in the tumors independent of tumor size.

TAMs were isolated from the 4T1 tumors at the experimental endpoint and it was found that the TAMs in emodin-treated mice had significantly decreased expression of IRF4 compared to those in control mice (FIG. 10D). IRF4 has previously been shown to play a major role in macrophage M2 activation and is regulated by removal of H3K27 tri-methylation (H3K37m3) by histone demethylase JMJD3. It was found that emodin significantly decreased the expression of JMJD3 in TAMs (FIG. 10D). Therefore emodin's effect on H3K27m3 was further examined using ChIP-qPCR and it was found that emodin significantly increased H3K27m3 levels on the IRF4 promoter but not on the CEBPβ promoter (FIG. 10E). Taken together, these results indicate that emodin inhibited M2 like polarization in TAMs through epigenetically blocking IRF4, STATE, and C/EBPβ signaling pathways in the breast cancer TME.

The effects of emodin on the response of macrophages to tumor cell-derived factors were examined. Peritoneal macrophages from C57Bl/6 mice were treated with EO771 TCM, and gene expression was examined by qPCR. Emodin dose-dependently inhibited TCM-induced expression of Arg1 and transcription factors C/EBPβ and IRF4 (FIG. 11A). Emodin also decreased the expression of CSFr1 (FIG. 11A), a key receptor on macrophages through which they are induced by tumor-secreted CSF1 towards M2-like activation. Moreover, emodin inhibited expression of MMP2 and MMP9 (FIG. 11A), which have been shown to promote tumor growth through remodeling the extra cellular matrix. Interestingly, it was also found that TCM treatment increased expression of ICAM1 in macrophages, and the effect was dose dependently blocked by emodin, suggesting that emodin could interfere with macrophage adhesion to tumor cells or other cell types in the tumor. In agreement with the in vivo data, TCM treatment increased the expression of JMJD3, and emodin significantly attenuated the increase (FIG. 11B). Both TCM and emodin had no effects on global levels of H3K27 methylation (FIG. 11C). However, TCM decreased H3K27m3 on the promoters of IRF4, Arg1, and C/EBPβ; and emodin treatment reversed the reduction (FIG. 11D). These results indicate that emodin epigenetically inhibits macrophage M2-like polarization in response to tumor-derived soluble factors.

TAMs substantially contribute to the immunosuppressive microenvironment in tumors. Since emodin inhibited TAM infiltration and M2-like polarization, it was hypothesized that emodin treatment would lead to increased T cell activation in breast tumors. T cells were detected in the draining lymph nodes of mice bearing 4T1 tumors using flow cytometry. Emodin treated mice had increased activated CD4+ and CD8+ T cells (FIG. 12A). There was a similar trend of increased activated T cells in the tumors of emodin treated mice (FIG. 12B). CD3+ cells were then isolated from the tumors and analyzed them using qPCR. T cells from emodin treated mice had a two-fold increase in IFNγ expression compared to those from control mice (FIG. 12C). Taken together, these data indicate that emodin treatment led to increased T cell activation in breast tumors.

The effect of emodin increase on activated T cells in breast tumors was examined through its effects on TAMs. Peritoneal macrophages were pre-treated with EO771 TCM with or without emodin for 24 h. Then the macrophages were incubated 1:1 with T cells stimulated with CD3/CD20 beads for 24 h. TCM treated macrophages reduced expression of activation marker CD69 by 70% on CD4 T cells compared to control macrophages; however, pre-treatment of macrophages with emodin along with TCM completely blocked the suppression of T cell activation and even increased CD69 expression on CD4 T cells above that of T cells co-cultured with control macrophages (FIG. 12D). T cell proliferation was examined after 72 h by CSFE depletion analysis and revealed that TCM and emodin co-treated macrophages restored T cell proliferation which was suppressed by TCM only-treated macrophages (FIG. 12E).

The effect of emodin on angiogenesis in tumors was examined by staining tumor sections with mouse endothelial antigen CD31 to detect microvessel density. Emodin significantly decreased CD31 staining in EO771 tumors to almost 50% of that in control (FIG. 12F). Taken together, these data indicate that by regulating TAM infiltration and polarization, emodin was able to increase T cell activation and suppress angiogenesis in breast cancer.

EO771 and 4T1 cells were treated with emodin in vitro and cell viability (LDH method) and proliferation (Ki67 staining) was determined. The results showed that emodin had low toxicity toward the two cell lines used. There was only a slight effect on cell viability starting at 25 μM (FIG. 13A) and no significant effect on cell proliferation at concentrations less than 50 μM (FIG. 13B). The effects of emodin on tumor cell gene expression were then examined. Emodin significantly inhibited the expression of chemoattractant and growth factors MCP1, CSF1, and CSF2 in both 4T1 and EO771 cells (FIG. 13C). Emodin treatment also significantly inhibited tumor cell expression of Thy1 (FIG. 13D), which has been shown to help anchor macrophages to the tumor cells. These results indicate that emodin could interfere with the ability of tumor cells to signal to, attract, and polarize macrophages.

Emodin was examined to determine if it can inhibit tumor cell induction of macrophage migration. Conditioned medium was collected from tumor cells treated with various concentrations of emodin, and the ability to induce macrophage migration was examined. There was a decrease in macrophage migration toward the TCM collected from cells treated with increasing concentrations of emodin (FIG. 14A). These results suggest that emodin inhibits the ability of breast cancer cells to attract macrophages.

Recent studies have shown that tumor cells can use juxtacrine signaling to communicate with macrophages and induce them toward a pro-tumor phenotype. Therefore, the effects of emodin on tumor cell-macrophage adhesion were examined by pre-treating macrophages, tumor cells, or both with emodin. It was found that emodin treatment of either macrophages or tumor cells significantly inhibited the adhesion of macrophages to a monolayer of tumor cells, and treatment of both macrophages and tumor cells decreased the adhesion even further (FIG. 14B).

Example 3

Breast tumor cells were isolated from the tumors of MMTV-PyMT mice (on a C57Bl/6 background) and treated with emodin. qPCR analysis showed that emodin significantly suppressed the expression of many genes, including CCL2 (a strong chemoattractant for macrophages), CSF1 (a molecule that may promote macrophage proliferation and also a chemoattractant for macrophages), CD90 (also known as Thy1; it mediates macrophage adhesion to tumor cells, and is also a marker for CSCs in PyMT tumors and human breast cancer), N-cadherin and vimentin (two markers of breast cancer cell epithelial mesenchymal transition, and FoxC2 and KLF4 (two transcription factors that control cancer stem cell formation and maintenance) (FIG. 15). These data suggest that emodin may 1) attenuate the ability of breast cancer cells to attract, migrate to, and adhere to macrophages by reducing the expression of key chemoattractant molecules and adhesion molecules, and 2) inhibit breast cancer epithelial mesenchymal transition and cancer stem cell formation and maintenance.

Example 4

Figure 16:
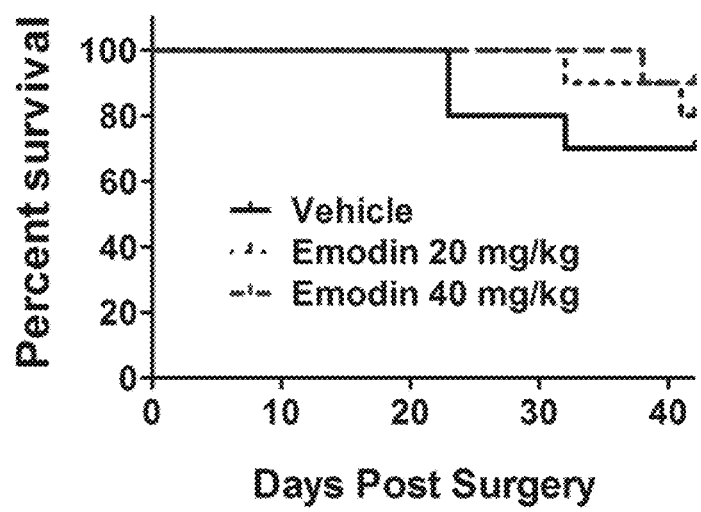
FIG. 16 illustrates the survival rates of control, high emodin dose treated and low emodin dose treated tumor carrying mice after the primary tumors were removed.

A cohort of 30 8-week-old, female BALB/c mice were injected with $2\times10^5$ 4T1 cells suspended in 20 µL PBS in each of their fourth mammary fat pads. The mice were randomly divided into three groups with 10 mice in each group. On day 10, tumors had reached a volume of 100-200 $mm^3$, and were surgically removed. The tumor volumes were not significantly different among the three groups. Post-surgical treatment began on day 11. This treatment involved each of the three groups receiving 800 µL daily IP injections of one of the following mixtures: PBS with 2% DMSO by volume (Control group), PBS with 1% DMSO by volume and 1% by volume of 50 mg/mL emodin in DMSO, or PBS with 2% by volume of 50 mg/mL emodin in DMSO. These two emodin solutions resulted in dosages of approximately 20 mg/kg (low emodin dose group) and 40 mg/kg (high emodin dose group), respectively. Daily IP emodin injections were administered until day 24; from day 25 to day 41, emodin was administered every other day. During the 41 days after the tumor removal, 3 mice in the control group died, while 2 mice and 1 mouse died in low emodin group and high emodin group, respectively (FIG. 16). Histology examination showed the dead mice all died of lung metastatic recurrence of breast cancer.

Figure 17:
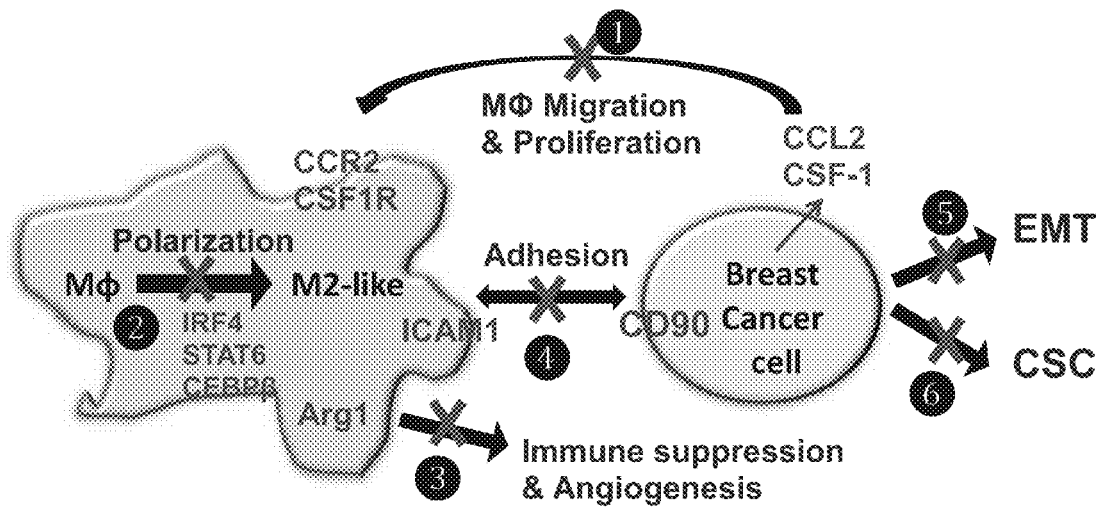
FIG. 17 presents a flow diagram showing how emodin interferes with tumor cell-macrophage interactions and thus inhibits breast cancer growth. "X"s indicate the functions of emodin, including 1) suppressing M2-like polarization of TAMs by targeting signaling through IRF4, STATE, and CEBPβ, 2) mitigating the immunosuppressive and pro-angiogenic activities of TAMs, 3) decreasing the expression and secretion of MCP-1 and CSF-1 in breast cancer cells, thus reducing the migration of macrophages towards cancer cells, 4) decreasing the expression of ICAM-1 in TAMs and the expression of Thy-1 (CD90) in breast cancer cells, thereby blocking the adhesion between the two cell types, 5) suppressing tumor cell epithelial-to-mesenchymal transition (EMT), and 6) inhibiting cancer stem cell (CSC) formation and maintenance.

Taken together, this data as well as that of the examples described above illustrate that emodin may effectively halt all steps in breast cancer development, including initiation, growth, metastasis, recurrence and therapy-resistance by disrupting the breast cancer cell-macrophage crosstalk as shown in FIG. 17.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for promoting macrophage homeostasis comprising delivering emodin to an area that includes macrophages and at least one macrophage phenotype inducing stimulus, the emodin suppressing the response of the macrophages to the stimulus and restoring or maintaining homeostasis of the macrophages between different macrophage phenotypes.

2. The method of claim 1, wherein the at least one macrophage phenotype inducing stimulus comprises an M1 or an M2 phenotype inducing stimulus.

3. The method of claim 1, wherein the at least one macrophage phenotype inducing stimulus comprises both an M1 and an M2 phenotype inducing stimulus.

4. The method of claim 1, the area comprising cancer cells.

5. The method of claim 1, the at least one macrophage phenotype inducing stimulus comprising one or more of a Th1 cytokine, a bacterial product, a Th2 cytokine, a growth factor, or a glucocorticoid.

6. The method of claim 1, wherein the method is carried out in vivo, the subject suffering from multiple different macrophage related pathologies.

7. The method of claim 6, wherein the area comprises a wound.

8. A method for suppressing or inhibiting macrophage response to a phenotype inducing stimulus, the method comprising:
  delivering emodin to an area that includes macrophages and a first phenotype inducing stimulus;
  following the delivery, exposing the macrophages to a second phenotype inducing stimulus; wherein
  upon the exposure to the second phenotype inducing stimulus, the macrophages exhibit a suppressed or inhibited response to the second phenotype inducing stimulus as compared to non-emodin treated macrophages.

9. The method of claim 8, wherein the first phenotype inducing stimulus comprises IFNγ.

10. The method of claim 8, wherein delivery of the emodin to the area comprising the first phenotype inducing stimulus inhibits recruit of transcription promoting histone markers to the promoter or enhancer regions of one or more genes of the macrophage.

11. The method of claim 10, wherein the transcription promoting histone markers include H3K27me3 or H3K27ac.

12. The method of claim 8, wherein the first phenotype inducing stimulus and the second phenotype inducing stimulus include the same compound.

13. The method of claim 8, wherein the first phenotype inducing stimulus and the second phenotype inducing stimulus include different compounds.

14. A method for suppressing or inhibiting macrophage migration, the method comprising delivering emodin to an area that includes macrophages, cancer cells, and at least one M2 phenotype inducing stimulus, wherein upon the delivery the macrophage is inhibited from activating to the M2 phenotype and migration of the macrophages toward the cancer cells is suppressed or inhibited.

15. The method of claim 14, wherein the cancer cells comprise breast cancer cells.

16. The method of claim 14, wherein adhesion between the macrophages and the cancer cells is also inhibited upon the delivery of the emodin.

17. The method of claim 14, wherein the method is an in vivo method.

18. The method of claim 17, the method further increasing T cell activation in the area.

19. The method of claim 17, wherein the cancer cells are breast cancer tumor cells, the method further inhibiting angiogenesis in the tumor.

20. The method of claim 17, the method further comprising delivering the emodin in conjunction with a chemotherapy.

* * * * *